(12) United States Patent
Rajagopal et al.

(10) Patent No.: US 11,123,187 B2
(45) Date of Patent: Sep. 21, 2021

(54) TRANSCATHETER ATRIAL ANCHORS AND METHODS OF IMPLANTATION

(71) Applicant: OPUS MEDICAL THERAPIES, LLC, Atlanta, GA (US)

(72) Inventors: Vivek Rajagopal, Atlanta, GA (US); Jaime Eduardo Sarabia, Mableton, GA (US); Yenchin Liao, Cary, NC (US)

(73) Assignee: OPUS MEDICAL THERAPIES, LLC, Atlanta, GA (US)

( * ) Notice: Subject to any disclaimer, the term of this patent is extended or adjusted under 35 U.S.C. 154(b) by 246 days.

(21) Appl. No.: 16/136,506

(22) Filed: Sep. 20, 2018

(65) Prior Publication Data

US 2019/0015205 A1   Jan. 17, 2019

Related U.S. Application Data

(63) Continuation-in-part of application No. 15/943,971, filed on Apr. 3, 2018, now Pat. No. 10,820,992, and (Continued)

(51) Int. Cl.
*A61F 2/24* (2006.01)
*A61B 18/00* (2006.01)
(Continued)

(52) U.S. Cl.
CPC ........ *A61F 2/2436* (2013.01); *A61B 17/0401* (2013.01); *A61B 18/00* (2013.01);
(Continued)

(58) Field of Classification Search
CPC . A61F 2/24–2496; A61B 17/0401–2017/0464
See application file for complete search history.

(56) References Cited

U.S. PATENT DOCUMENTS 4,242,715 A   12/1980   Laird
4,337,496 A   6/1982   Laird
(Continued)

FOREIGN PATENT DOCUMENTS

AU   2016202264 A1   11/2016
CA   3 059 102 A1   10/2018
(Continued)

OTHER PUBLICATIONS

International Search Report and Written Opinion in corresponding International application No. PCT/US2018/025971 dated Jul. 10, 2018.
(Continued)

*Primary Examiner* — Tan-Uyen T Ho
*Assistant Examiner* — Charles M Wei
(74) *Attorney, Agent, or Firm* — FisherBroyles, LLP; Rachel H. Huffstetler

(57) ABSTRACT

Anchor assemblies for endovascular introduction and implantation for tethering a replacement heart valve to a cardiac wall. An anchor delivery system introduces the assembly. The anchor may be either implanted with a tether connected thereto or implanted and then connected to a tether. If the latter, a tether assembly is mounted to the implanted anchor to connect the anchor to the valve. The anchors may be implanted into any cardiac wall including the interventricular septum or the epicardial space and the valve may replace the mitral or tricuspid valve.

22 Claims, 30 Drawing Sheets

Related U.S. Application Data a continuation-in-part of application No. 15/943,792, filed on Apr. 3, 2018, now Pat. No. 10,820,991, said application No. 15/943,971 is a continuation-in-part of application No. 15/943,792, filed on Apr. 3, 2018, now Pat. No. 10,820,991.

(60) Provisional application No. 62/481,846, filed on Apr. 5, 2017, provisional application No. 62/509,587, filed on May 22, 2017, provisional application No. 62/558,315, filed on Sep. 13, 2017.

(51) Int. Cl.
*A61B 17/04* (2006.01)
*A61B 18/14* (2006.01)
*A61M 25/09* (2006.01)
*A61B 17/00* (2006.01)

(52) U.S. Cl.
CPC ........ *A61B 18/1492* (2013.01); *A61F 2/2412* (2013.01); *A61F 2/2427* (2013.01); *A61F 2/2457* (2013.01); *A61B 2017/00243* (2013.01); *A61B 2017/00247* (2013.01); *A61B 2017/00477* (2013.01); *A61B 2017/042* (2013.01); *A61B 2017/044* (2013.01); *A61B 2017/0409* (2013.01); *A61B 2017/0417* (2013.01); *A61B 2017/0427* (2013.01); *A61B 2017/0443* (2013.01); *A61B 2017/0464* (2013.01); *A61B 2018/00351* (2013.01); *A61B 2018/144* (2013.01); *A61F 2220/0016* (2013.01); *A61F 2220/0075* (2013.01); *A61F 2250/0096* (2013.01); *A61M 25/09041* (2013.01)

(56) References Cited

U.S. PATENT DOCUMENTS

| | | | |
|---|---|---|---|
| 4,746,057 A | 5/1988 | Wagner | |
| 4,830,360 A | 5/1989 | Carr, Jr. | |
| 5,079,776 A | 1/1992 | Crawford | |
| 5,312,438 A * | 5/1994 | Johnson | A61B 17/0401 606/104 |
| 5,569,306 A * | 10/1996 | Thal | A61F 2/0811 606/232 |
| 5,662,704 A * | 9/1997 | Gross | A61F 2/2412 623/2.1 |
| 5,683,451 A * | 11/1997 | Lenker | A61F 2/91 623/1.11 |
| 5,706,520 A | 1/1998 | Thornton et al. | |
| 5,849,004 A * | 12/1998 | Bramlet | A61B 17/0401 606/232 |
| 6,042,583 A * | 3/2000 | Thompson | A61B 17/06109 606/232 |
| 6,093,162 A | 7/2000 | Fairleigh et al. | |
| 7,530,995 B2 | 5/2009 | Quijano et al. | |
| 7,780,725 B2 | 8/2010 | Salahieh et al. | |
| 8,147,542 B2 * | 4/2012 | Maisano | A61B 17/0401 623/2.11 |
| 8,236,049 B2 | 8/2012 | Takei et al. | |
| 8,252,050 B2 * | 8/2012 | Maisano | A61F 2/2457 623/2.11 |
| 8,273,973 B2 | 9/2012 | Kimmons et al. | |
| 8,333,155 B2 | 12/2012 | Cylvick | |
| 8,403,983 B2 | 3/2013 | Quadri et al. | |
| 8,449,599 B2 | 5/2013 | Chau | |
| 8,489,165 B2 | 7/2013 | Segman | |
| 8,545,553 B2 * | 10/2013 | Zipory | A61F 2/2451 623/2.37 |
| 8,549,175 B2 | 10/2013 | Krishna | |
| 8,690,939 B2 * | 4/2014 | Miller | A61F 2/2457 623/2.11 |
| 8,728,155 B2 | 5/2014 | Montorfano et al. | |
| 8,790,394 B2 * | 7/2014 | Miller | A61B 17/0401 623/2.1 |
| 8,888,843 B2 | 11/2014 | Khairkhahan et al. | |
| 8,900,295 B2 * | 12/2014 | Migliazza | A61B 17/0401 623/2.19 |
| 8,932,348 B2 | 1/2015 | Solem et al. | |
| 8,998,976 B2 | 4/2015 | Gregg et al. | |
| 9,005,084 B2 | 4/2015 | Silagy et al. | |
| 9,033,383 B2 | 5/2015 | Rampersad | |
| 9,034,033 B2 * | 5/2015 | McLean | A61F 2/2445 623/2.12 |
| 9,078,749 B2 | 7/2015 | Lutter et al. | |
| 9,375,312 B2 | 6/2016 | Weber | |
| 9,439,763 B2 | 9/2016 | Geist et al. | |
| 9,441,832 B2 | 9/2016 | Bushee | |
| 9,474,605 B2 | 10/2016 | Rowe et al. | |
| 9,480,559 B2 * | 11/2016 | Vidlund | A61L 27/34 |
| 9,486,306 B2 | 11/2016 | Tegels et al. | |
| 9,578,982 B2 | 2/2017 | Rampersad | |
| 9,827,092 B2 * | 11/2017 | Vidlund | A61B 17/0401 |
| 9,849,001 B2 | 12/2017 | Thompson, Jr. et al. | |
| 9,895,221 B2 * | 2/2018 | Vidlund | A61F 2/2418 |
| 9,986,993 B2 * | 6/2018 | Vidlund | A61F 2/2457 |
| 10,039,639 B2 | 8/2018 | Marchand et al. | |
| 2004/0138707 A1 * | 7/2004 | Greenhalgh | A61B 17/0401 606/232 |
| 2004/0190383 A1 | 9/2004 | Marcucelli et al. | |
| 2005/0075727 A1 * | 4/2005 | Wheatley | A61F 2/2457 623/2.17 |
| 2005/0137697 A1 * | 6/2005 | Salahieh | A61F 2/2439 623/2.11 |
| 2006/0235509 A1 * | 10/2006 | Lafontaine | A61F 2/2436 623/2.11 |
| 2006/0241656 A1 | 10/2006 | Sterksen et al. | |
| 2006/0241745 A1 | 10/2006 | Solem | |
| 2007/0118151 A1 * | 5/2007 | Davidson | A61B 17/0625 606/144 |
| 2007/0142838 A1 * | 6/2007 | Jordan | A61B 17/0642 606/75 |
| 2007/0277279 A1 | 12/2007 | Battat | |
| 2008/0125860 A1 | 5/2008 | Webler | |
| 2009/0276040 A1 * | 11/2009 | Rowe | A61F 2/2454 623/2.18 |
| 2010/0016655 A1 * | 1/2010 | Annest | A61B 17/00234 600/37 |
| 2011/0004296 A1 * | 1/2011 | Lutter | A61F 2/2445 623/1.26 |
| 2011/0011917 A1 * | 1/2011 | Loulmet | A61B 17/0401 227/181.1 |
| 2011/0224785 A1 | 9/2011 | Hacohen | |
| 2011/0301698 A1 | 12/2011 | Miller et al. | |
| 2012/0078360 A1 | 3/2012 | Rafiee | |
| 2012/0136430 A1 | 5/2012 | Sochman et al. | |
| 2013/0023985 A1 * | 1/2013 | Khairkhahan | A61L 27/042 623/2.38 |
| 2013/0116780 A1 * | 5/2013 | Miller | A61F 2/2448 623/2.36 |
| 2013/0172978 A1 * | 7/2013 | Vidlund | A61F 2/2439 623/1.12 |
| 2013/0184811 A1 * | 7/2013 | Rowe | A61F 2/2418 623/2.11 |
| 2013/0190861 A1 | 7/2013 | Chau et al. | |
| 2013/0211508 A1 | 8/2013 | Lane et al. | |
| 2013/0282059 A1 | 10/2013 | Ketai et al. | |
| 2013/0282110 A1 | 10/2013 | Schweich, Jr. et al. | |
| 2013/0304197 A1 | 11/2013 | Buchbinder et al. | |
| 2013/0331929 A1 | 12/2013 | Mitra et al. | |
| 2014/0005778 A1 | 1/2014 | Buchbinder et al. | |
| 2014/0031928 A1 * | 1/2014 | Murphy | A61F 2/2418 623/2.18 |
| 2014/0163668 A1 | 6/2014 | Rafiee | |
| 2014/0296972 A1 | 10/2014 | Tegels et al. | |
| 2014/0316516 A1 | 10/2014 | Vidlund et al. | |
| 2014/0379076 A1 | 12/2014 | Vidlund et al. | |
| 2015/0142103 A1 | 5/2015 | Vidlund | |
| 2015/0250590 A1 | 9/2015 | Gries et al. | |

(56) References Cited

U.S. PATENT DOCUMENTS

| | | | |
|---|---|---|---|
| 2015/0366556 A1* | 12/2015 | Khairkhahan | A61B 17/0401 606/232 |
| 2015/0366666 A1 | 12/2015 | Khairkhahan et al. | |
| 2016/0022501 A1 | 1/2016 | Schultz et al. | |
| 2016/0120646 A1 | 5/2016 | Dwork et al. | |
| 2016/0213467 A1 | 7/2016 | Backus et al. | |
| 2016/0262878 A1 | 9/2016 | Backus et al. | |
| 2016/0262881 A1* | 9/2016 | Schankereli | A61F 2/2418 |
| 2016/0310268 A1* | 10/2016 | Oba | A61F 2/2418 |
| 2016/0317305 A1 | 11/2016 | Pelled et al. | |
| 2016/0324635 A1 | 11/2016 | Vidlund et al. | |
| 2016/0367360 A1 | 12/2016 | Cartledge et al. | |
| 2017/0143478 A1 | 5/2017 | Schwartz et al. | |
| 2017/0172737 A1 | 6/2017 | Kuetting et al. | |
| 2017/0209293 A1 | 7/2017 | Combs | |
| 2017/0227320 A1 | 8/2017 | Derousse | |
| 2017/0312078 A1 | 11/2017 | Krivoruchko | |
| 2018/0085215 A1 | 3/2018 | Vaturi et al. | |
| 2018/0289473 A1* | 10/2018 | Rajagopal | A61F 2/2418 |
| 2018/0289474 A1* | 10/2018 | Rajagopal | A61F 2/2418 |
| 2018/0289485 A1* | 10/2018 | Rajagopal | A61F 2/2457 |
| 2018/0318071 A1 | 11/2018 | Lozonschi et al. | |
| 2019/0015205 A1* | 1/2019 | Rajagopal | A61F 2/2457 |
| 2020/0001135 A1 | 1/2020 | Rajagopal | |

FOREIGN PATENT DOCUMENTS

| | | |
|---|---|---|
| CA | 3 059 106 A1 | 10/2018 |
| CN | 103826750 A | 5/2014 |
| CN | 105658178 B | 6/2016 |
| CN | 106618798 A1 | 5/2017 |
| DE | 10 2012 002 785 A1 | 8/2013 |
| EP | 1 462 880 A2 | 9/2004 |
| EP | 1 462 880 A3 | 4/2005 |
| EP | 3311774 A1 | 4/2018 |
| KR | 10-2020-0007805 A | 1/2020 |
| KR | 10-2020-0007806 A | 1/2020 |
| UY | 37667 A | 10/2018 |
| UY | 37668 A | 10/2018 |
| WO | 1994/020049 A1 | 9/1994 |
| WO | 2005/094711 A2 | 10/2005 |
| WO | WO2014021905 A1 | 2/2014 |
| WO | 2016050751 A1 | 4/2016 |
| WO | 2016168609 A1 | 10/2016 |
| WO | 2016/179427 A1 | 11/2016 |
| WO | 2016186909 A1 | 11/2016 |
| WO | DM/098 100 S | 6/2017 |
| WO | 2017/117560 A1 | 7/2017 |
| WO | 2018/187390 A1 | 10/2018 |
| WO | 2018/187495 A1 | 10/2018 |
| WO | 2020/005527 A1 | 1/2020 |

OTHER PUBLICATIONS

International Search Report and Written Opinion in corresponding International application No. PCT/PCT/US2018/026118 dated Jun. 15, 2018.

Toyama et al. Mitral annular motion in patients after transcatheter MitraClip and mitral valve surgery; Echocardiography 2017; 34: 334-339.

Boudjemline Y, Agnoletti G, Bonnet D, et al. Steps toward the percutaneous replacement of atrioventricular valves an experimental study. Journal of the American College of Cardiology 2005;46:360-5.

Bai Y, Chen HY, Zong GJ, et al. Percutaneous establishment of tricuspid regurgitation: an experimental model for transcatheter tricuspid valve replacement. Chinese medical journal 2010;123:806-9.

Laule M, Stangl V, Sanad W, Lembcke A, Baumann G, Stangl K. Percutaneous transfemoral management of severe secondary tricuspid regurgitation with Edwards Sapien XT bioprosthesis: first-in-man experience. Journal of the American College of Cardiology 2013;61:1929-31.

Lauten A, Doenst T, Hamadanchi A, Franz M, Figulla HR. Percutaneous bicaval valve implantation for transcatheter treatment of tricuspid regurgitation: clinical observations and 12-month follow-up. Circulation Cardiovascular interventions 2014;7:268-72.

Lauten A, Ferrari M, Hekmat K, et al. Heterotopic transcatheter tricuspid valve implantation: first-in-man application of a novel approach to tricuspid regurgitation. European heart journal 2011;32:1207-13.

Lauten A, Figulla HR, Unbehaun A, et al. Interventional Treatment of Severe Tricuspid Regurgitation: Early Clinical Experience in a Multicenter, Observational, First-in-Man Study. Circulation Cardiovascular interventions 2018;11:e006061.

Lauten A, Figulla HR, Willich C, et al. Percutaneous caval stent valve implantation: investigation of an interventional approach for treatment of tricuspid regurgitation. European heart journal 2010;31:1274-81.

Lauten A, Laube A, Schubert H, et al. Transcatheter treatment of tricuspid regurgitation by caval valve implantation-experimental evaluation of decellularized tissue valves in central venous position. Catheterization and cardiovascular interventions : official journal of the Society for Cardiac Angiography & Interventions 2014.

Figulla HR, Kiss K, Lauten A. Transcatheter interventions for tricuspid regurgitation—heterotopic technology: TricValve. EuroIntervention : journal of EuroPCR in collaboration with the Working Group on Interventional Cardiology of the European Society of Cardiology 2016;12:Y116-8.

Barbanti M, Ye J, Pasupati S, El-Gamel A, Webb JG. The Helio transcatheter aortic dock for patients with aortic regurgitation. EuroIntervention : journal of EuroPCR in collaboration with the Working Group on Interventional Cardiology of the European Society of Cardiology 2013;9 Suppl:S91-4.

Hahn RT, Meduri CU, Davidson CJ, et al. Early Feasibility Study of a Transcatheter Tricuspid Valve Annuloplasty: SCOUT Trial 30-Day Results. Journal of the American College of Cardiology 2017;69:1795-806.

Rosser BA, Taramasso M, Maisano F. Transcatheter interventions for tricuspid regurgitation: TriCinch (4Tech). EuroIntervention : journal of EuroPCR in collaboration with the Working Group on Interventional Cardiology of the European Society of Cardiology 2016;12:Y110-2.

Stephan von Bardeleben R, Tamm A, Emrich T, Munzel T, Schulz E. Percutaneous transvenous direct annuloplasty of a human tricuspid valve using the Valtech Cardioband. European heart journal 2017;38:690.

Kuwata S, Taramasso M, Nietlispach F, Maisano F. Transcatheter tricuspid valve repair toward a surgical standard: first-in-man report of direct annuloplasty with a cardioband device to treat severe functional tricuspid regurgitation. European heart journal 2017.

Rogers J. Transcatheter TR solution 6: Millipede. Transcatheter Cardiovascular Therapeutics; 2017 Nov. 1, 2017; Denver, Colorado.

Parada-Campelo F, Perlman G, Philippon F, et al. First-in-Man Experience of a Novel Transcatheter Repair System for Treating Severe Tricuspid Regurgitation Journal of the American College of Cardiology 2015;66:2475-83.

Nickenig G, Kowalski M, Hausleiter J, et al. Transcatheter Treatment of Severe Tricuspid Regurgitation With the Edge-to-Edge MitraClip Technique. Circulation 2017;135:1802-14.

Cao P. Catheter-Based Tricuspid Valve Replacement via Right Atrium: An Animal Experimental Study. Transcatheter Cardiovascular Therapeutics; 2017; Denver, Colorado.

Navia JL, Kapadia S, Elgharably H, et al. First-in-Human Implantations of the NaviGate Bioprosthesis in a Severely Dilated Tricuspid Annulus and in a Failed Tricuspid Annuloplasty Ring. Circulation Cardiovascular interventions 2017;10.

Regueiro, et al. Transcatheter Mitral Valve Replacement: Insights From Early Clinical Experience and Future Challenges; JACC vol. 69, No. 17, 2017; May 2, 2017: 2175-92.

Non-Final Office Action received for U.S. Appl. No. 15/943,792 dated Jan. 8, 2020, 50 pages.

International Search Report and Written Opinion of the International Searching Authority dated Aug. 30, 2019, in International Application No. PCT/US19/36428.

Non-Final Office Action received for U.S. Appl. No. 15/943,971 dated Jan. 8, 2020, 49 pages.

(56) References Cited

OTHER PUBLICATIONS

International Search Report and Written Opinion issued in corresponding International Application No. PCT/US2019/057145 dated Dec. 31, 2019.
International Preliminary Report on Patentability received for PCT Application Serial No. PCT/US2018/025971 dated Oct. 17, 2019, 9 pages.
International Preliminary Report on Patentability received for PCT Application Serial No. PCT/US2018/026118 dated Oct. 17, 2019, 11 pages.
Supplementary European Search Report dated Apr. 30, 2021 in corresponding European Publication No. 3606443.
Supplementary European Search Report dated Mar. 21, 2019 in corresponding European Publication No. 3606444.

* cited by examiner

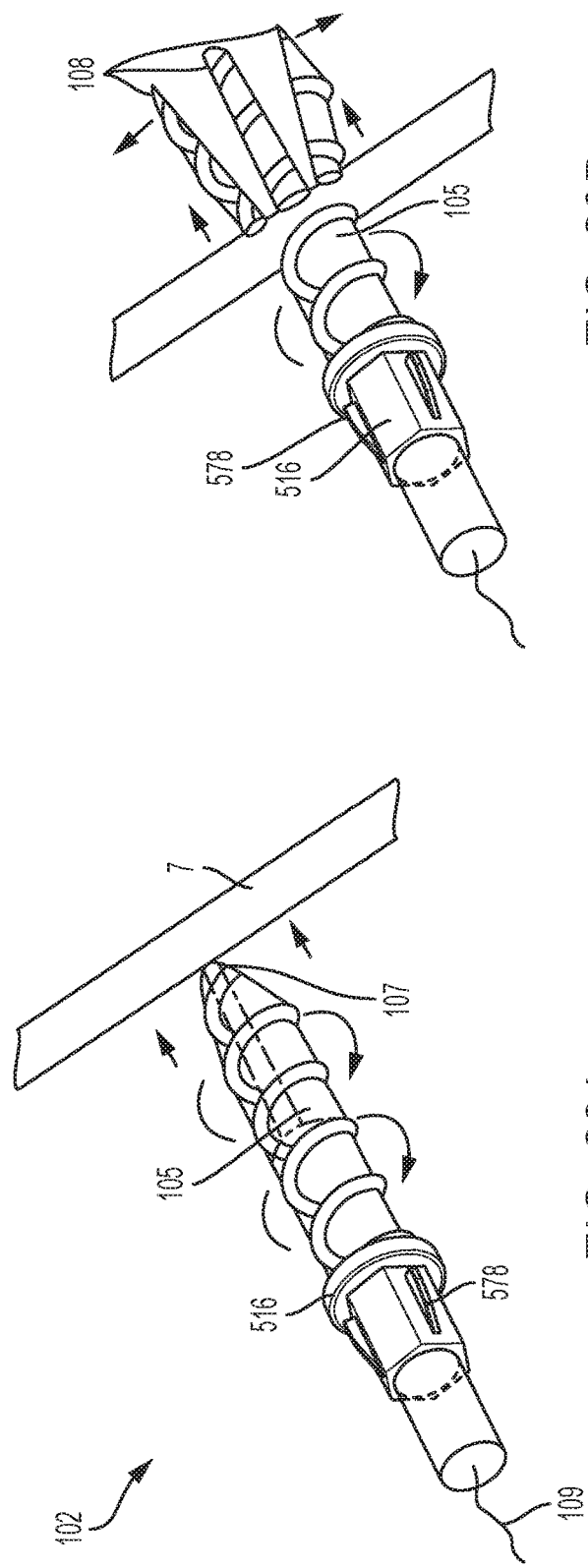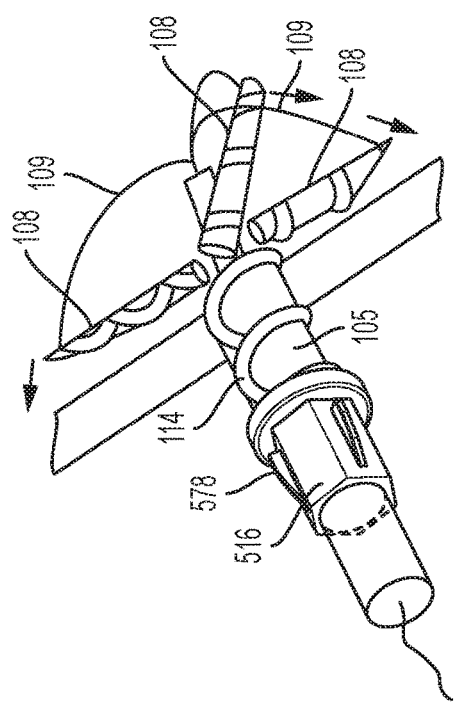

TRANSCATHETER ATRIAL ANCHORS AND METHODS OF IMPLANTATION

CROSS REFERENCE TO RELATED APPLICATIONS

The application is a continuation-in-part of U.S. patent app. Ser. No. 15/943,971 (Filed Apr. 3, 2018) and a continuation-in-part of U.S. patent application Ser. No. 15/943, 792 (filed Apr. 3, 2018), both of which claim the benefit of and priority to Provisional Patent Application Ser. Nos. 62/481,846 (filed Apr. 5, 2017), 62/509,587 (filed May 22, 2017), and 62/558,315 (filed Sep. 13, 2017), the disclosures of all are herein incorporated by reference.

FIELD OF THE INVENTION

The present invention relates generally to medical devices and systems that are implanted minimally invasively in the heart and methods of implantation of these devices and systems. More specifically, the invention pertains to intracardiac anchors for anchoring medical devices, such as cardiac valves, to a cardiac wall, including for interventricular or epicardial implantation of a replacement valve into an intracardial wall.

BACKGROUND OF THE INVENTION

Transcatheter valves have proven safe and effective for the replacement of native cardiac valves. These valves have been tested extensively for replacement of aortic, mitral, and pulmonic valves, but replacement of tricuspid valves remains challenging given the complex and delicate anatomy to which prostheses must attach. Limiting paravalvular regurgitation of transcatheter mitral and tricuspid valves is challenging because the mitral and tricuspid annuli are complex saddle-shaped structures that are highly dynamic during the cardiac cycle. Compounding this difficulty for the tricuspid valve is the frequent presence of intracardiac leads in patients with significant tricuspid regurgitation (TR). Because ventricular leads traverse the annulus from the right atrium to the right ventricle, a transcatheter tricuspid valve must seal around both the annulus and the lead to limit regurgitation in these patients.

Applicant's Ser. No. 15/943,792 discloses a Transcatheter Anchor and Tether Devices, Systems and Methods of Implantation including an anchor delivery system for introducing a tether coupled to the anchor and a valve delivery system for delivering, positioning and sealing the valve. Applicant's Ser. No. 15/943,792 is directed to a Transcatheter Anchor and Tether Devices, Systems and Methods of Implantation wherein, the anchor delivery system comprises an anchor which is implanted and not initially coupled to a tether. The disclosure presented herein may be used in connection with either of these delivery or anchoring systems, or any delivery or anchoring systems and may be used for anchoring any valve, including that disclosed in Applicant's Ser. No. 15/974,696.

SUMMARY OF THE INVENTION

The application relates to anchors for tethering a replacement heart valve for replacing a native heart valve. According to various aspects, the anchor is implanted into a cardiac wall utilizing an anchor delivery system. The anchor may be either implanted with a tether connected thereto or implanted and then connected to a tether. If the latter, a tether assembly is mounted to the implanted anchor to connect the anchor to the valve. According to various aspects, the anchors may be implanted into any cardiac wall including the interventricular septum or the epicardial space and the valve may replace the mitral or tricuspid valve.

The anchor includes an anchor cap and an anchor screw for implanting into the cardiac wall. The tether is coupled to the anchor cap either directly or with a tether assembly. According to one aspect, the anchor extends through to an opposing side of a cardiac wall, such as the pericardial space or the interventricular septum. According to other aspects, the anchor screw penetrates the cardiac wall a sufficient depth without penetrating the wall to the opposing side. According to another aspect, the anchor includes an anchor shaft formed or more than one shaft members which expand within the cardiac wall Other apparatuses, methods, systems, features, and advantages of the medical devices and systems that are implanted minimally invasively in the heart will be or become apparent to one with skill in the art upon examination of the following figures and detailed description. It is intended that all such additional apparatuses, methods, systems, features, and advantages be included within this description, be within the scope of the medical devices and systems that are implanted minimally invasively in the heart and be protected by the accompanying claims.

BRIEF DESCRIPTION OF THE DRAWINGS

FIG. 29A-29C are perspective views of an anchor according to an alternative aspect with a splitting or expanding anchor screw;

DETAILED DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "tether" includes aspects having two or more tethers unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The application relates to medical devices and systems to be minimally invasively implanted in the heart and methods of implantation of these devices and systems. More specifically, the application relates to intracardiac anchors 75 and methods and systems for endovascularly introducing and implanting the anchor 75 to a cardiac wall such as for implanting a valve 100 in the heart which is tethered to the anchor 75 to replace the native valve.

Figure 1:
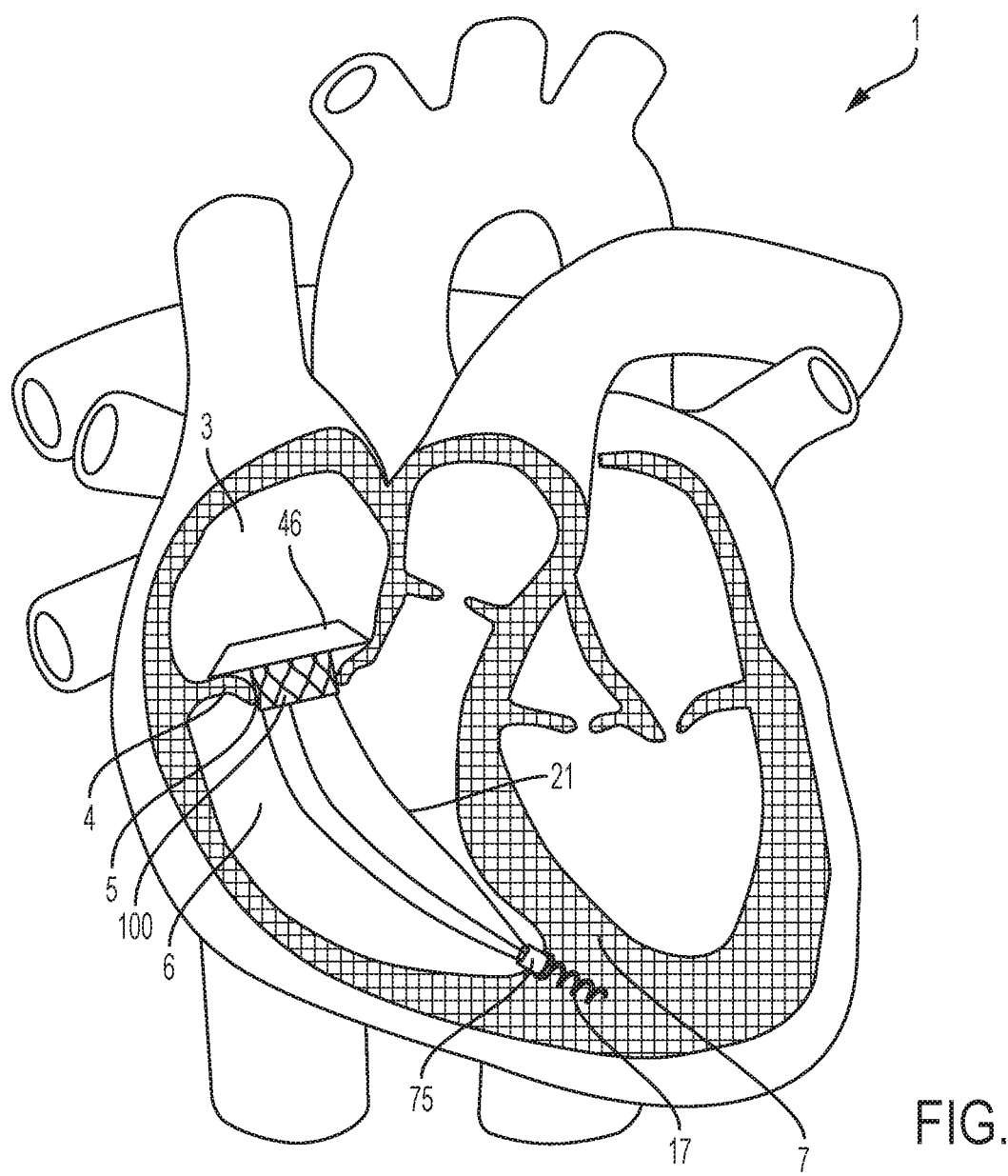
FIG. 1 is a cut-away perspective view of a heart showing the transcatheter atrial sealing skirt system positioned across the tricuspid valve in the heart.
Figure 2:
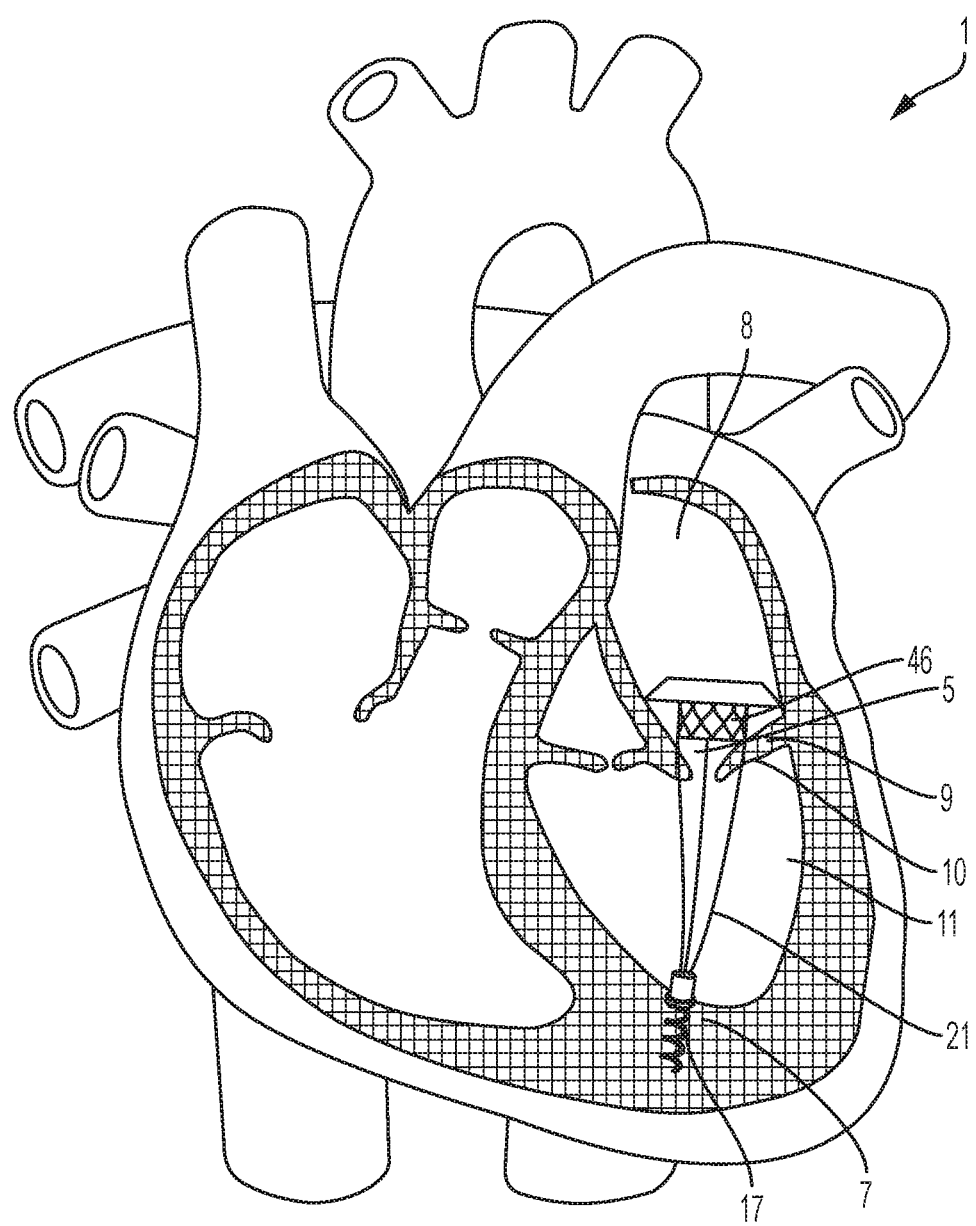
FIG. 2 is a cut-away perspective view of a heart showing the transcatheter atrial sealing skirt system positioned across the mitral valve in the heart.

The disclosure herein relates anchors 75 and anchor delivery assemblies for implanting minimally invasively in the heart 1 and methods of implantation. FIG. 1 illustrates the transcatheter valve 100 which has been implanted to replace the native tricuspid valve (for example) according the medical assembly disclosed herein. FIG. 2 illustrates the valve 100 implanted to replace the native mitral valve. The heart, of course, includes the right atrium 3, right atrial floor 4, right ventricle 6, intracardiac wall 7, left atrium 8 and left ventricle 11. The replacement valve 100 is positioned at the deployment site 5. As shown and described, by way of example, the anchoring systems are used to anchor a transcatheter valve 100 which may, include an atrial sealing skirt 46 configured to couple to the atrial floor. At least one tether 21, composed of one or more cords, connects the valve 100 to the anchor 75 as shown. The tether 21 may be implanted by anchor 75 to any intracardiac wall, including, but not limited to, the interventricular septum, ventricular apex, or ventricular free wall. For the sake of discussion only, the ventricular apex is shown but it is within the spirit and scope of the present invention to anchor the tether 75 to any intracardiac wall.

Also, a tethering assembly cooperates with the anchor 75 connecting the valve 100 to the anchor 75. For example, the anchors disclosed herein may be used in connection with a valve 100 which includes a sealing skirt 46 for cooperating with the valve 100 to conform to the respective atrial floor to prevent paravalvular regurgitation of prosthesis as disclosed in Applicant's Ser. No. 15/974,696. Various aspects of the anchors 75 disclosed herein may be implanted with a tether pre-assembled to the anchor or independent of the tether wherein the tether is applied to the anchor after implantation. The anchors described herein may be employed to anchor a tricuspid valve or mitral valve as shown in FIGS. 1 and 2, respectively.

Figure 3:
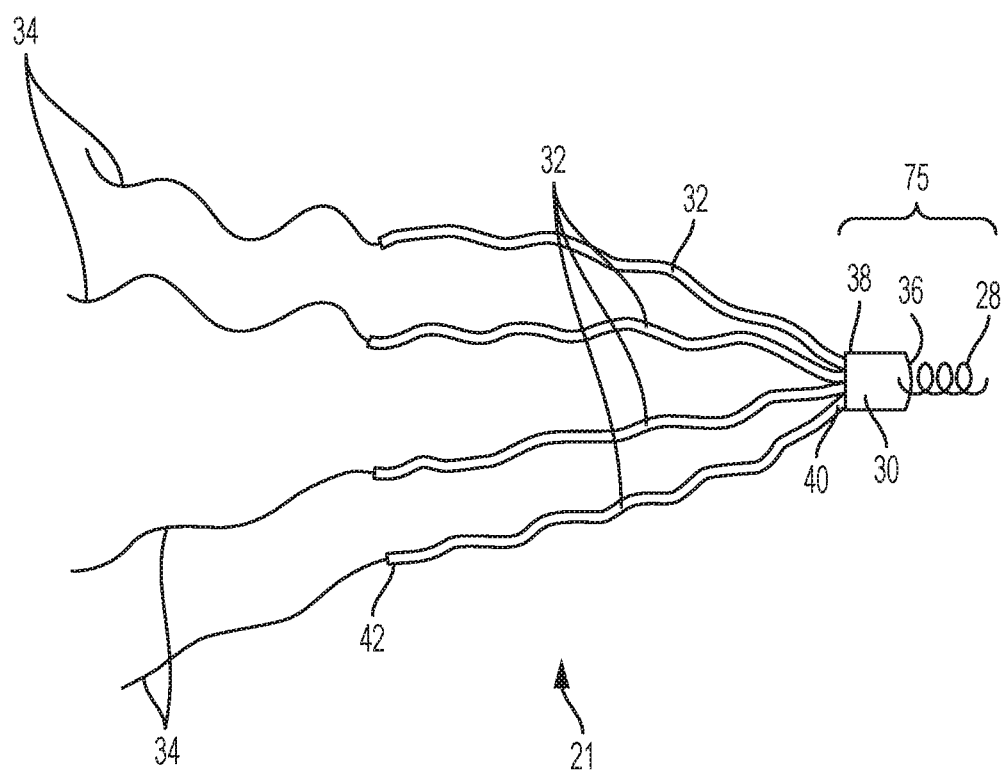
FIG. 3 is a side elevational view of a tether, with its cords fused to sutures, connected to an anchor, according to one aspect.
Figure 4A:
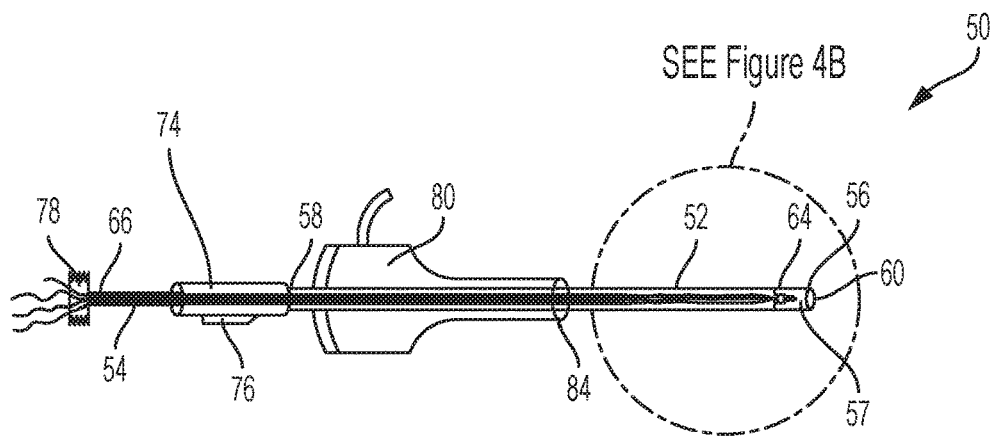
FIG. 4A is a side elevational view of an anchor delivery system, according to one aspect.

The Tether and Anchor (FIGS. 3-5)

Referring now to FIG. 3, at least one tether 21 and, as shown, composed of a plurality of cords 32, is/are operatively connected to the replacement valve 100 and connects the valve 100 to the anchor 75. The tether 21 includes at least one cord 32, and each cord 32 is connected to a suture 34. The anchor 75 includes an anchor screw 28 and an anchor cap 30. In one aspect, the anchor screw is coupled to and extends from a distal end 36 of the anchor cap, and the at least one cord 32 of the tether 21 is coupled to and extends from a proximal end 38 of the anchor cap 30. That is, the anchor cap 30 is positioned between the anchor screw 28 and the cord 32. The anchor screw 28, of anchor 75, is configured to securely attach the tether 21 to an intracardiac wall such as the ventricular apex 7 of the heart 1. For example, the anchor screw 28 is an active fixation screw comprising threads or a coil that is securely rotated into the ventricular apex. The anchor 75 and the anchor screw 28 are configured to securely attach the tether 21 to an intracardiac wall such as the ventricular apex 7 of the heart without extending through the apex and outside of the heart. Thus, in this aspect, substantially no portion of the assembly completely penetrates and/or extends completely through any portion of the heart wall, and trans-apical access is not necessary. In a further aspect (not shown), rather than the anchor screw 28, a fixation mechanism composed of, but not limited to, nitinol, stainless steel, cobalt-chromium, or titanium alloys, in the shape of barbs, hooks, prongs and the like is positioned at the distal end 36 of the anchor cap 30 to securely attach the tether 21 to the ventricular apex 7 of the heart 1 without extending through the apex and outside of the heart.

The at least one cord 32 has a distal end 40 coupled to a portion of the anchor cap 30 and a proximal end 42 coupled to the suture 34. In one aspect, the cord is a strong yet flexible cord such as, for example and without limitation, an expanded polytetrafluoroethylene (ePTFE) or ultra-high-molecular-weight polyethylene (UHMWPE or UHMW) cord. In use, described more fully below, a central portion of the cord 32 (between the distal end and the proximal end) extends through and/or is coupled to the valve 100 to hold the valve in the desired position relative to the tricuspid annulus.

The Anchor Delivery System

Referring now to FIGS. 4A-C, 5A and 5B, the anchor delivery system 50 for positioning and deploying the anchor cap 30 of anchor 75 at the desired implantation site is illustrated. The delivery system 50 comprises an anchor delivery guide 52 and an anchor delivery rod 54. In this aspect, the anchor delivery guide 52 has a distal end 56, an opposed proximal end 58 and an inner guide lumen 57 extending between the anchor delivery guide tip 60 and the opposed proximal end 58, and is configured so that at least a portion of the anchor delivery rod 54 extends therethrough. In another aspect, at least a portion of the anchor delivery guide 52 is flexible so that a tip 60 at the distal end of the anchor delivery guide 52 is positioned at or adjacent to an intracardiac wall anchoring site 62 such as the ventricular apex 7.

The anchor delivery rod 54 is configured to securely attach the anchor screw 28 to the anchoring site 62. The anchor delivery rod 54 has a distal end 64, an opposed proximal end 66 and an inner rod lumen 59 extending therebetween, the inner rod lumen 59 is sized and configured so that at least a portion of the at least one tether 21 is inserted therethrough. In another aspect, at least a portion of the anchor delivery rod 54 is flexible so that a rod tip 68 at the distal end of the anchor delivery rod 54 is positioned at or adjacent the intracardiac wall anchoring site 62 such as the ventricular apex 7.

Figure 4B:
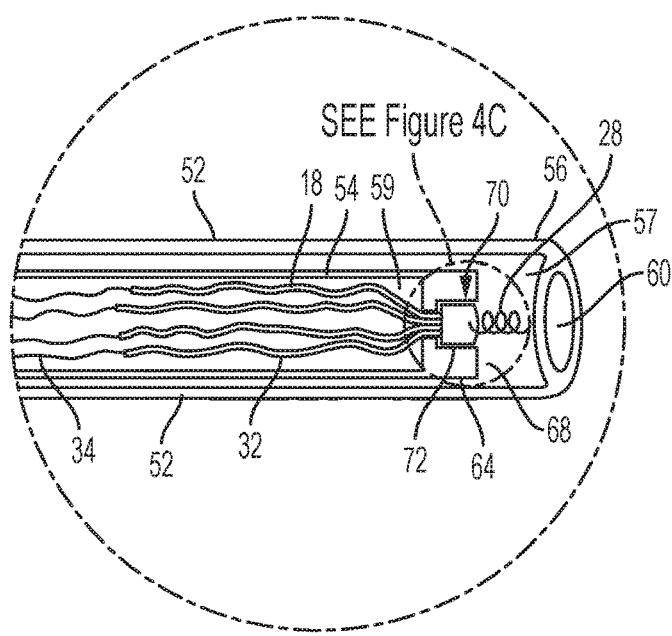
FIG. 4B is a magnified side elevational view of the anchor delivery system of FIG. 4A.
Figure 4C:
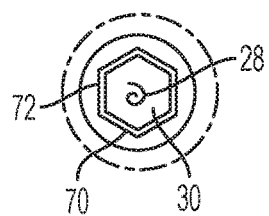
FIG. 4C is an end view of the anchor delivery system of FIG. 4A.

As shown in FIG. 4B, a bore or socket 70 is defined in the rod tip 68 of the anchor delivery rod 54. The socket is sized and configured to matingly engage the anchor cap 30 which includes a mating member such as an outer surface configuration which, as shown, in a hexagon. Other mating members or outer surface configurations may be employed. That is, at least a portion of the anchor cap is positioned in the socket 70 so that walls 72 of the socket engage the anchor cap. Thus, for example, when the anchor cap 30 is positioned in and engages the socket 70, rotation of the anchor delivery rod 54 rotates the anchor cap 30. Accordingly, the socket engages the anchor cap 30 and the anchor screw 28 extends distally from the anchor delivery rod 54 as illustrated in FIG. 4B. In a further aspect, when the socket 70 engages the anchor cap 30, the at least one cord 32 and at least a portion of the at least one suture 34 extends through the inner rod lumen of the anchor delivery rod 54.

The anchor delivery system 50 further comprises a guide handle 74 with a deflection knob 76 coupled to the anchor delivery guide 52. The guide handle and the deflection knob are configured and used to help guide the tip 60 of the anchor delivery guide to the intracardiac wall anchoring site 62 such as the ventricular apex 7. As shown in FIG. 4A, the anchor delivery system 50 includes a rod handle 78 coupled to the anchor delivery rod 54. In use, described more fully below, rotation of the rod handle 78 correspondingly rotates the rod tip 68 and the anchor cap 30 when the anchor cap 30 is received within the socket 70.

The anchor delivery system 50 includes a sheath 80 removably coupled to the anchor delivery guide 52. The sheath 80 is in fluid communication with the anchor delivery guide 52 so that fluids, such as carbon dioxide and the like surround the anchor delivery guide through the sheath. A central sheath channel 84 is defined by the sheath 80 that is in communication with the anchor delivery guide 52 so that the anchor delivery rod 54 and other system components extends through the central sheath channel 84.

Figure 5A:
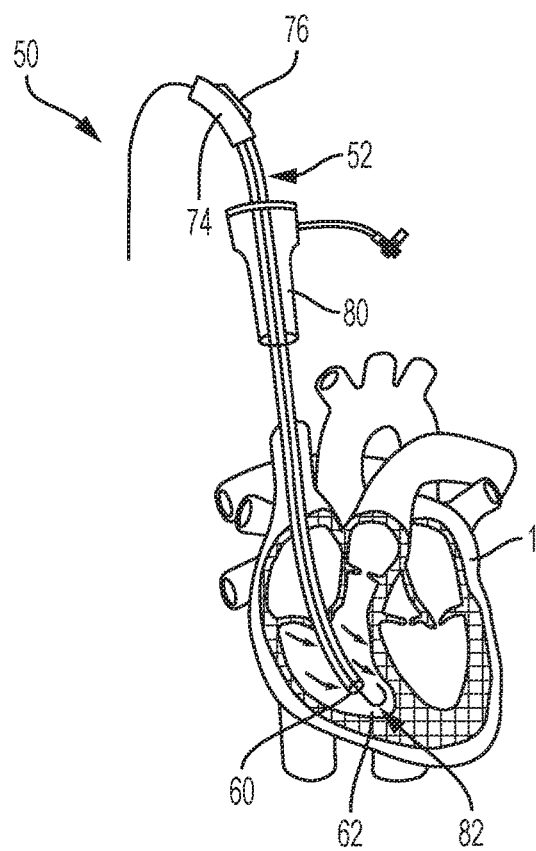
FIG. 5A is a perspective view of the anchor delivery system in which a portion of the device is positioned in the right ventricle.
Figure 5B:
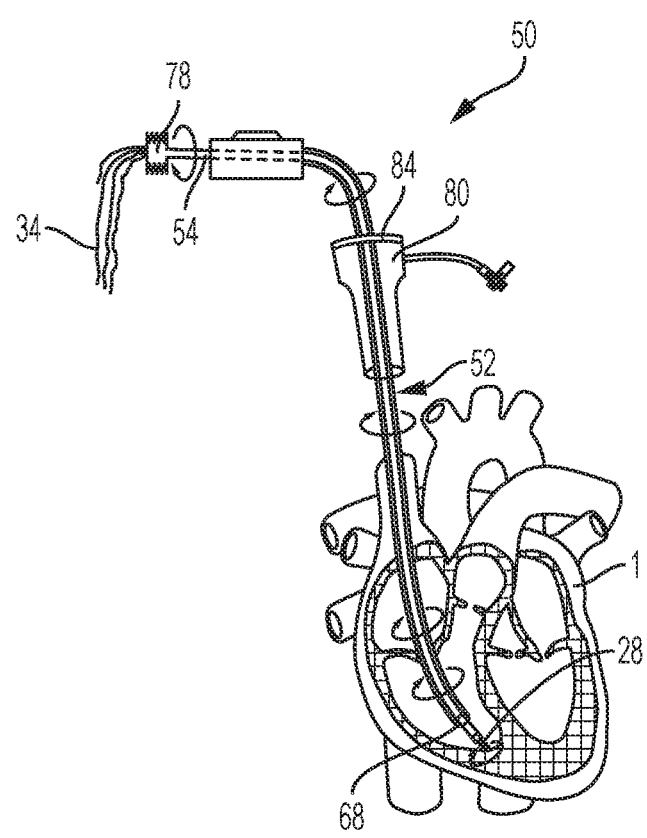
FIG. 5B is a perspective view of the anchor delivery in which the anchor delivery system is delivering a portion of the tether, connected to the anchor, into the right ventricle.

The anchor delivery system 50 optionally includes a J-wire 82, as shown in FIGS. 5A and 5B that is guidable by the user to the anchoring site 62. The J-wire is, for example and without limitation, a 0.025" or 0.035" J-wire. Of course, J-wires having other diameters are contemplated. As in any over-the-wire system, the J-wire is introduced first via sheath 80 into the right atrium 3, across the site of deployment 5, into the right ventricle 6, to the anchoring site 62. By providing a pathway for the anchor delivery guide 52 to track over to its final target, a J-wire increases the efficiency and safety of this step.

The Anchor Delivery Method

To install the valve 100 in the tricuspid annulus, as shown in FIG. 5A, the J-wire 82, serving as a guidewire, is inserted into the right internal jugular vein, enters the right atrium and approaches the anchor implantation site 62. The anchor delivery system 50 is guided by the user, along the length of the previously implanted J-wire 82, to the intracardiac wall anchoring site 62 such as the ventricular apex 7. The anchor delivery guide tip 60 at the distal end 56 of the anchor delivery guide 52 is positioned at or adjacent the anchoring site such as the ventricular apex. As shown in FIG. 5B the, anchor delivery rod 54 and the tether 21, connected to the anchor cap 30 and anchor screw 28 of the anchor 75, are positioned within the inner guide lumen 57 of the anchor delivery guide 52. The anchor cap 30 is coupled to the distal end 64 of the anchor delivery rod 54 with the cord 32 of the tether 21 positioned in the lumen 59 of the anchor delivery rod 54. The anchor delivery rod 54 is advanced distally through the inner guide lumen of the anchor delivery guide 52 until the anchor cap 30 coupled to the distal end of the anchor delivery rod 54 is positioned at or adjacent the intracardiac wall anchoring site 62 such as the ventricular apex 7.

Figure 6A:
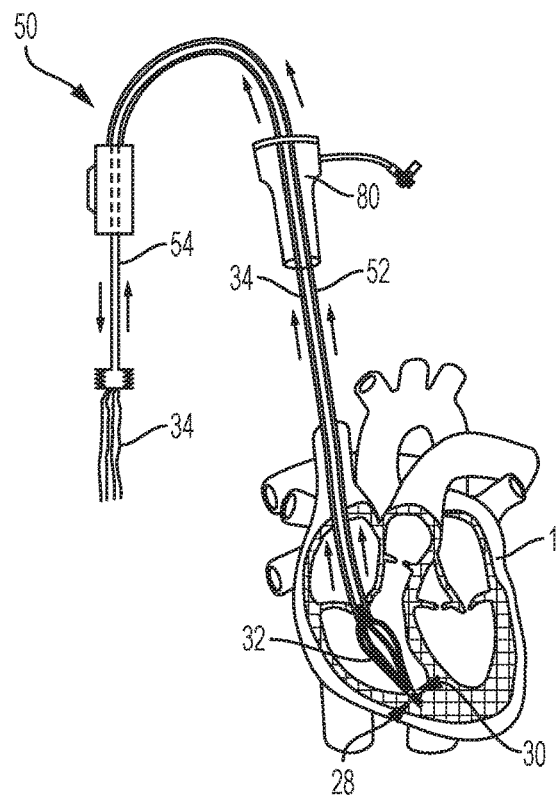
FIG. 6A is a perspective view of the anchor delivery system in which the anchor delivery system is delivering a portion of the tether, connected to the anchor into the right ventricle.

With the anchor screw 28 of the anchor 75, connected to tether 21 via anchor cap 30, positioned adjacent to the anchoring site 62, the proximal end 66 of the anchor delivery rod 54 is rotated to cause corresponding rotation of the anchor cap 30 as illustrated in FIG. 5B. For example, the rotating handle 78 is rotated in a first direction to cause corresponding rotation of the anchor cap. The anchor screw coupled to the anchor cap 30 also rotates and screws into a portion of the intracardiac wall anchoring site 62 such as the ventricular apex 7 until the distal end 36 of the anchor cap is adjacent to the intracardiac wall and/or the tether is securely attached thereto the wall. Note that in this position, the anchor screw 28 does not extend completely through any portion of the heart wall, and trans-apical access is not necessary. Upon placement of the anchor cap 30 in the desired position, the anchor delivery rod 54 and the anchor delivery guide 52 of the anchor delivery system 50 are retracted from the heart 1 as illustrated in FIG. 6A. As such, in FIG. 6B, the cords 32 of tether 21, coupled to the anchor cap 30, are secured by the anchor screw 28 of anchor 75, and remain within the right ventricle and the valve delivery system 100 is employed.

Figure 6B:
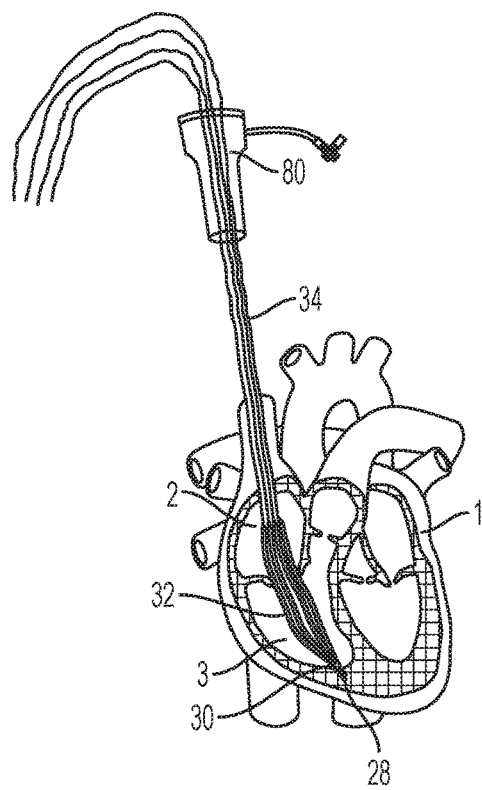
FIG. 6B is a perspective view of the tether, connected to the anchor, positioned in the right ventricle.

As shown in FIG. 6B, after placement of the anchor cap 30 of anchor 75, the at least one cord 32 of the tether 21 extends from the anchor cap through the tricuspid annulus and into the right atrium 2. A suture 34 is coupled to the proximal end of each cord and extends through the superior (or inferior) vena cava and out of the heart 1.

Figure 7A:
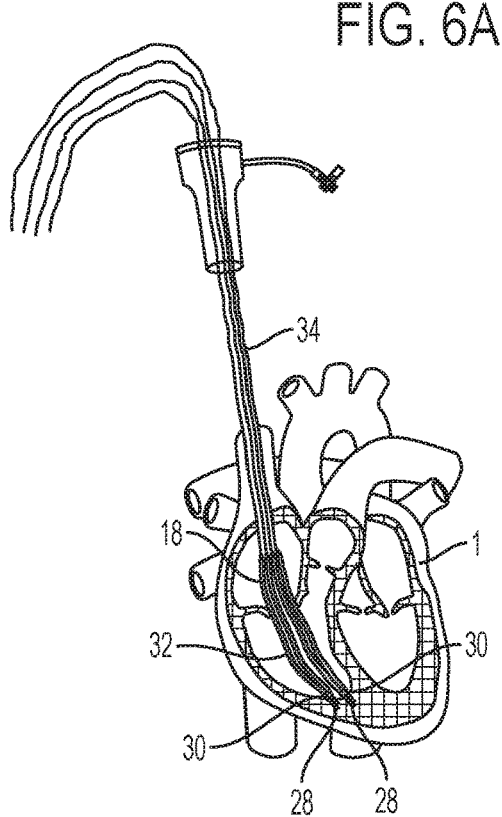
FIG. 7A is a perspective view of two tethers, each connected to an anchor positioned in a heart, according to one aspect.
Figure 7B:
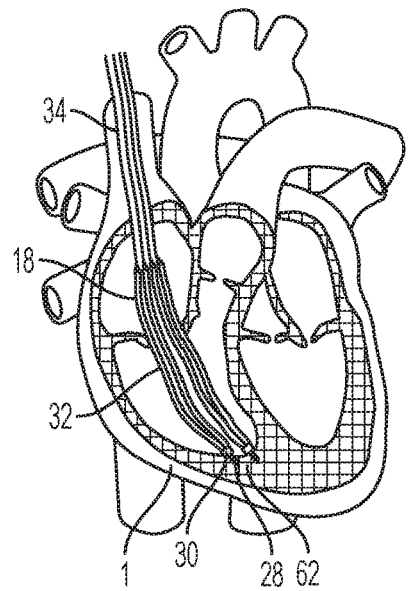
FIG. 7B is a magnified view of the two tethers each connected to an anchor of FIG. 7A.

If more than one tether 21, connected to an anchor 75, is delivered, each anchor 75 is secured by its anchor screw 28, and this process is repeated until all tethers, connected to anchors, have been securely attached to the heart wall. In one aspect and as illustrated in FIGS. 7A and 7B, the assembly 10 utilizes two anchors and tethers, three anchors and tethers, four anchors and tethers, or more anchors and tethers are also contemplated.

The Epicardial Tether System (FIGS. 8-15)

Figure 8:
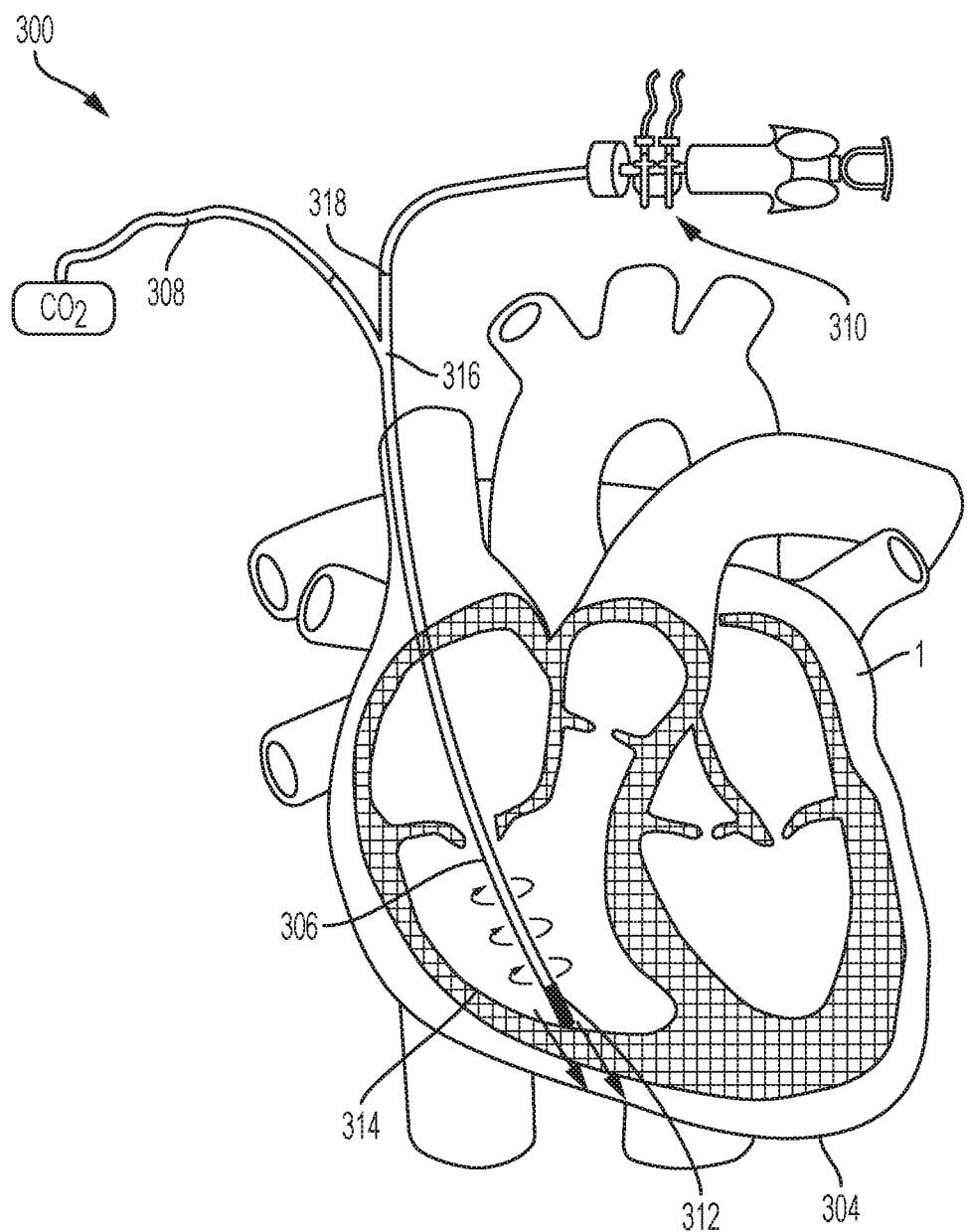
FIG. 8 is a perspective view of an epicardial tether system for positioning an anchor in the pericardial space, according to one aspect.

In another aspect, illustrated in FIGS. 8-15, the assembly comprises an epicardial tether system 300 for positioning an anchor 302 in the pericardial space 304. In one aspect, the epicardial tether comprises a catheter 306, a $CO_2$ gas line 308 and a manifold 310. In another aspect, the catheter is a micro-catheter having a distal end 312 configured to be screwed and/or otherwise urged through at least a portion of the wall of the heart 1. For example, and as illustrated in FIG. 8, the distal end of the micro-catheter engages the endocardium 314 of the heart. The micro-catheter 306 also has a proximal end 316 opposed to the distal end and an inner catheter lumen 318. The proximal end of the micro-catheter is coupled to the $CO_2$ gas line 308 and the manifold 310 so that the $CO_2$ gas line and the manifold are in sealed fluid communication with the inner catheter lumen.

Figure 9:
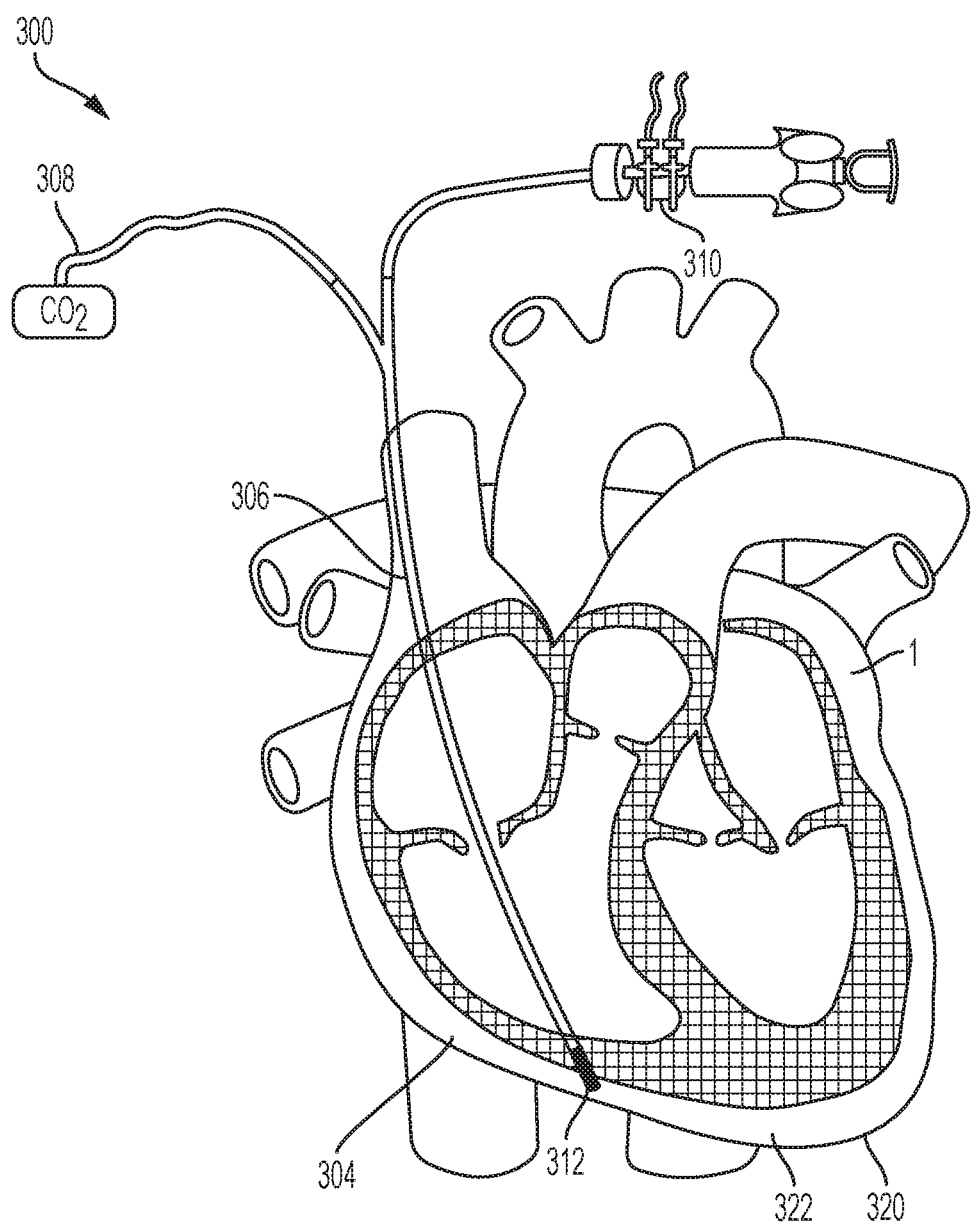
FIG. 9 is a perspective view of the epicardial tether system of FIG. 8, in which a portion of a catheter of the system has entered the pericardial space.

Referring now to FIG. 9, the distal end 312 of the micro-catheter 306 is urged through the heart wall until the distal end of the micro-catheter is positioned in the pericardial space 304 by the pericardium 320. In one aspect, a contrasting agent 322 is injected from the manifold 310 through the inner catheter lumen 318 and into the pericardial space to verify that the distal end 312 of the micro-catheter 306 is in the pericardial space 304.

Figure 10:
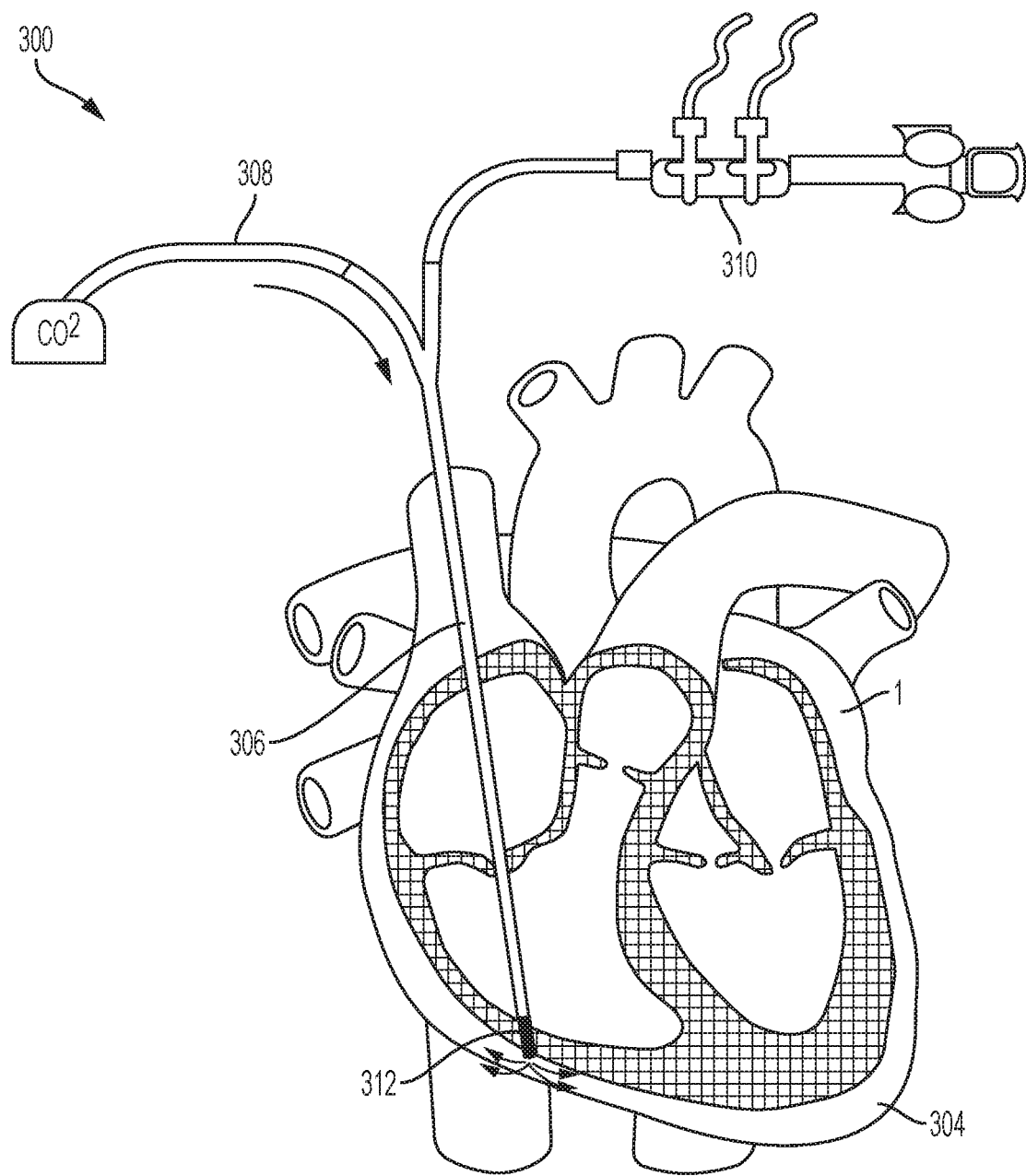
FIG. 10 is a perspective view of the epicardial tether system of FIG. 8, in which the pericardial space has been insufflated.

Once the distal end 312 of the micro-catheter 306 has been positioned in the pericardial space 304, carbon dioxide is injected from the $CO_2$ gas line 308 through the inner catheter lumen 318 and into the pericardial space 304 to insufflate the space, illustrated in FIG. 10.

Figure 11:
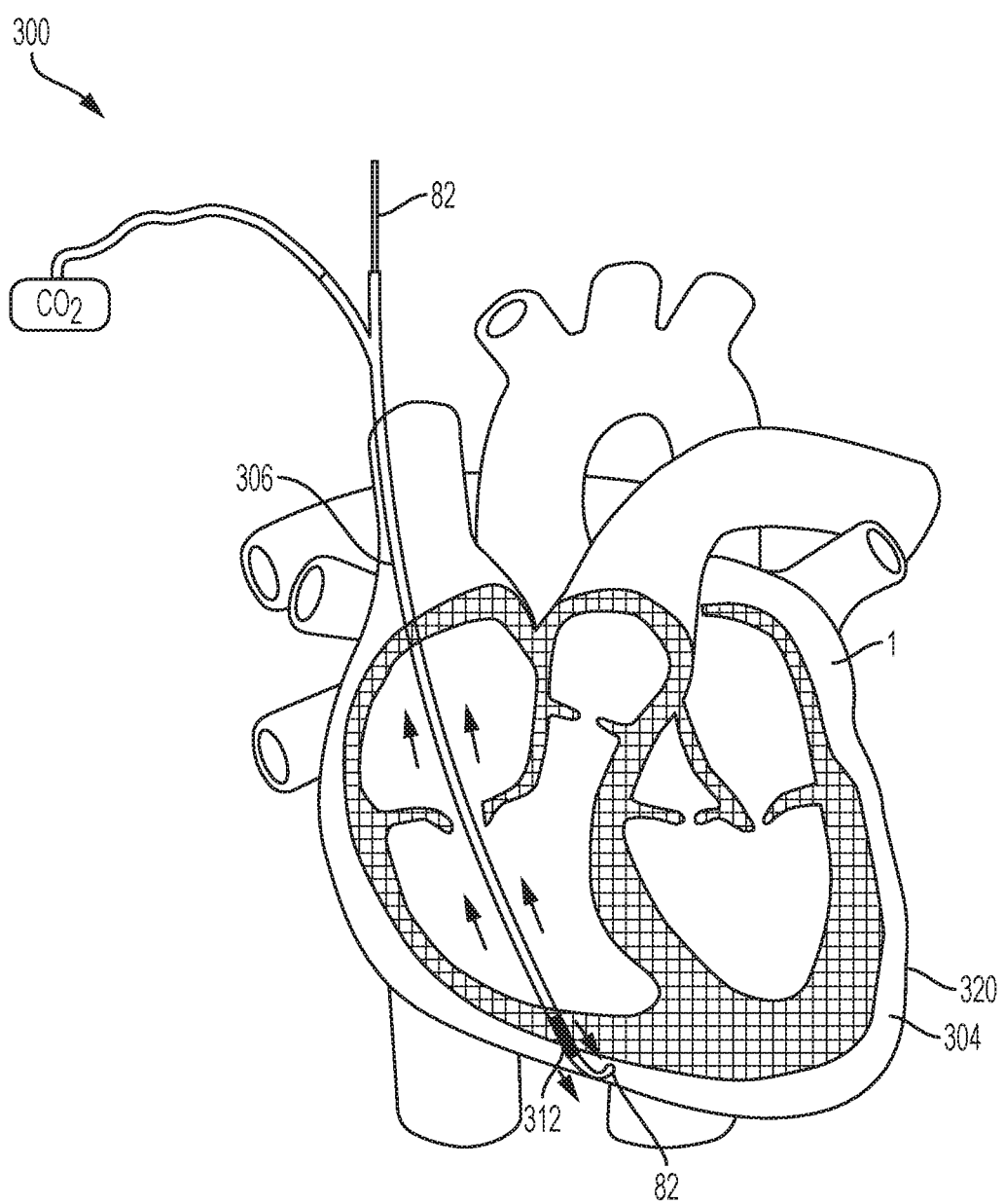
FIG. 11 is a perspective view of the epicardial tether system of FIG. 8, in which a J-wire has been inserted into the insufflated pericardial space.

In one aspect, the J-wire 82 is then advanced through the inner catheter lumen 318 and into the pericardial space 304 as illustrated in FIG. 11. With the J-wire in place, the catheter 306 is removed from the heart 1.

Figure 12:
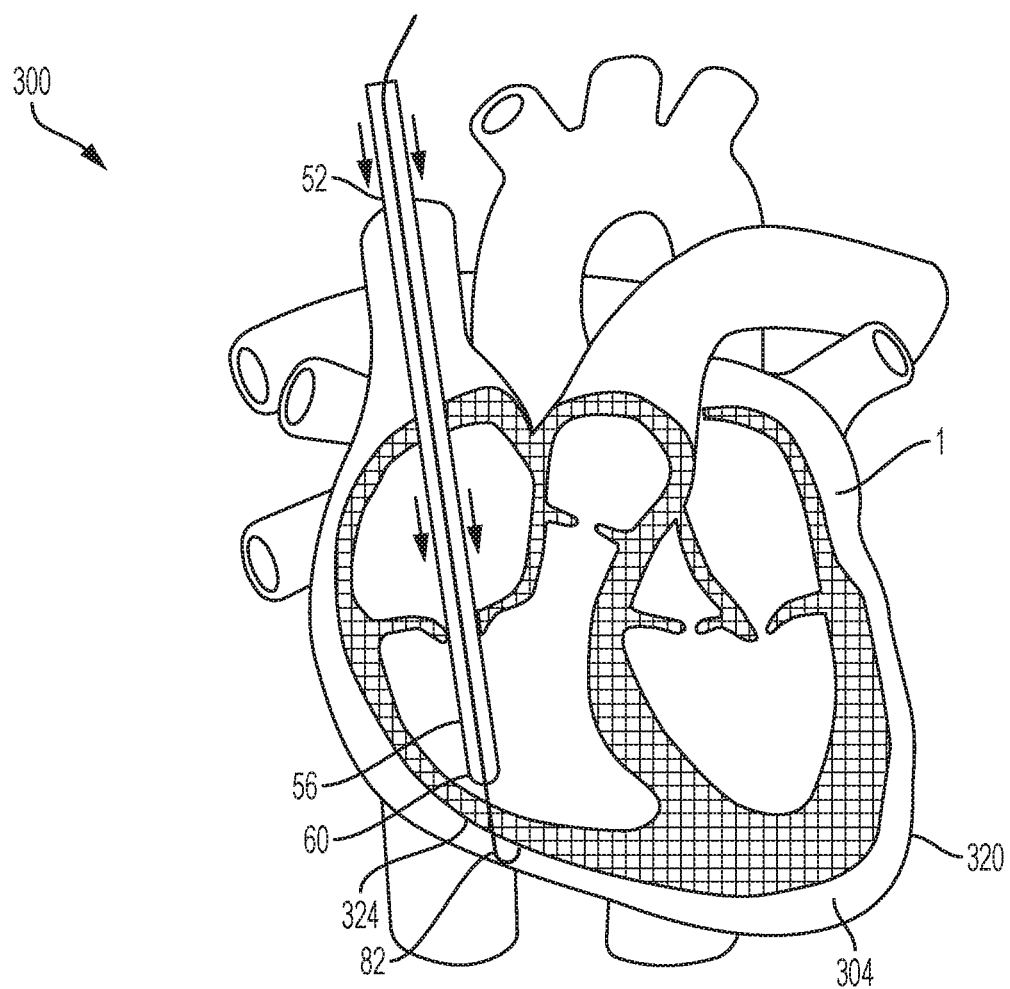
FIG. 12 is a perspective view of the epicardial tether system of FIG. 8, in which an anchor delivery guide of the system approaches the insufflated pericardial space.
Figure 13:
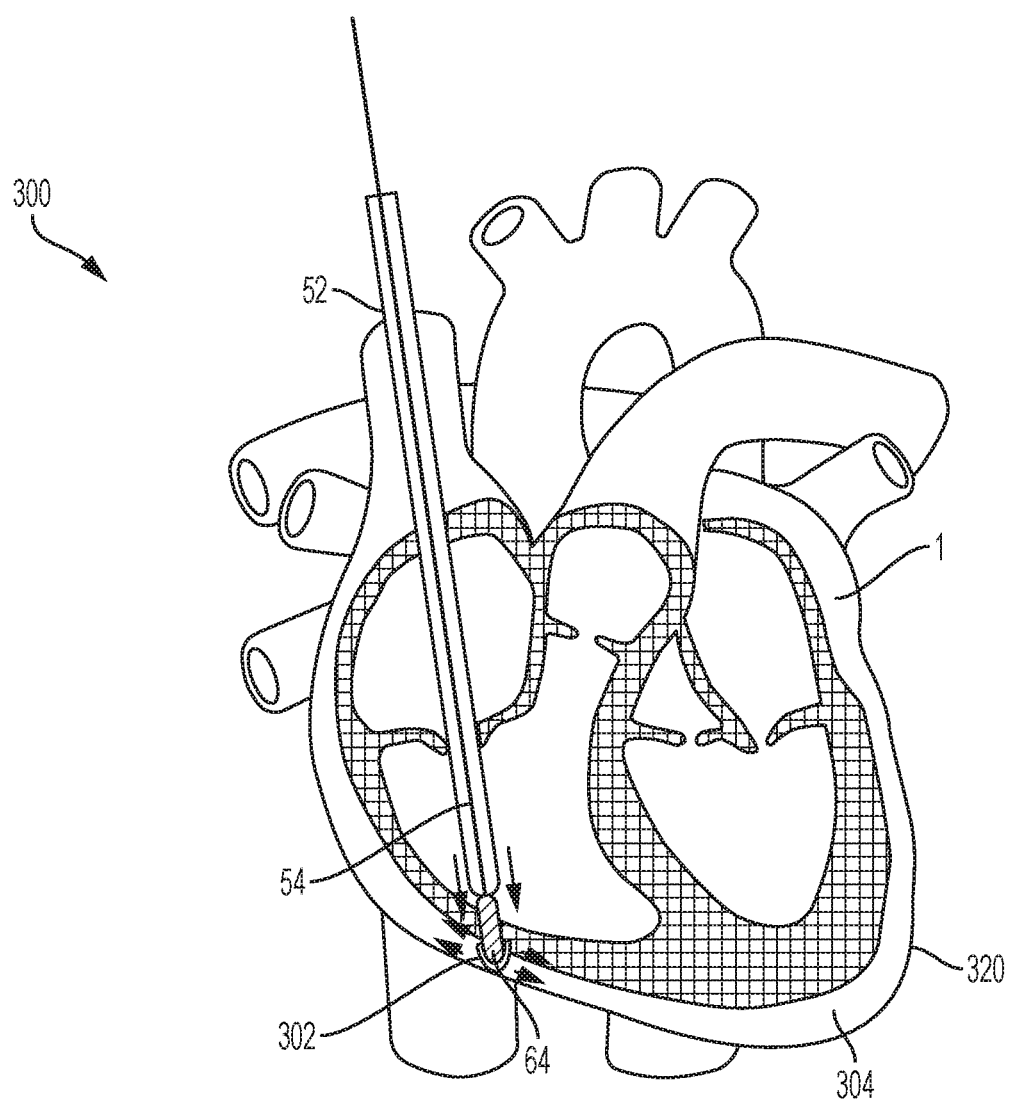
FIG. 13 is a perspective view of the epicardial tether system of FIG. 8, in which an anchor of the system is being positioned in the insufflated pericardial space.

In another aspect, illustrated in FIGS. 12 and 13, the anchor delivery guide 52 is inserted over the J-wire 82 until the tip 60 at the distal end 56 of the anchor delivery guide is positioned at or adjacent an anchoring site 324 in the pericardial space 304. The anchor delivery rod 54 is inserted through the inner guide lumen of the anchor delivery guide 52 until the distal end 64 of the anchor delivery rod is positioned in the pericardial space 304.

Figure 14:
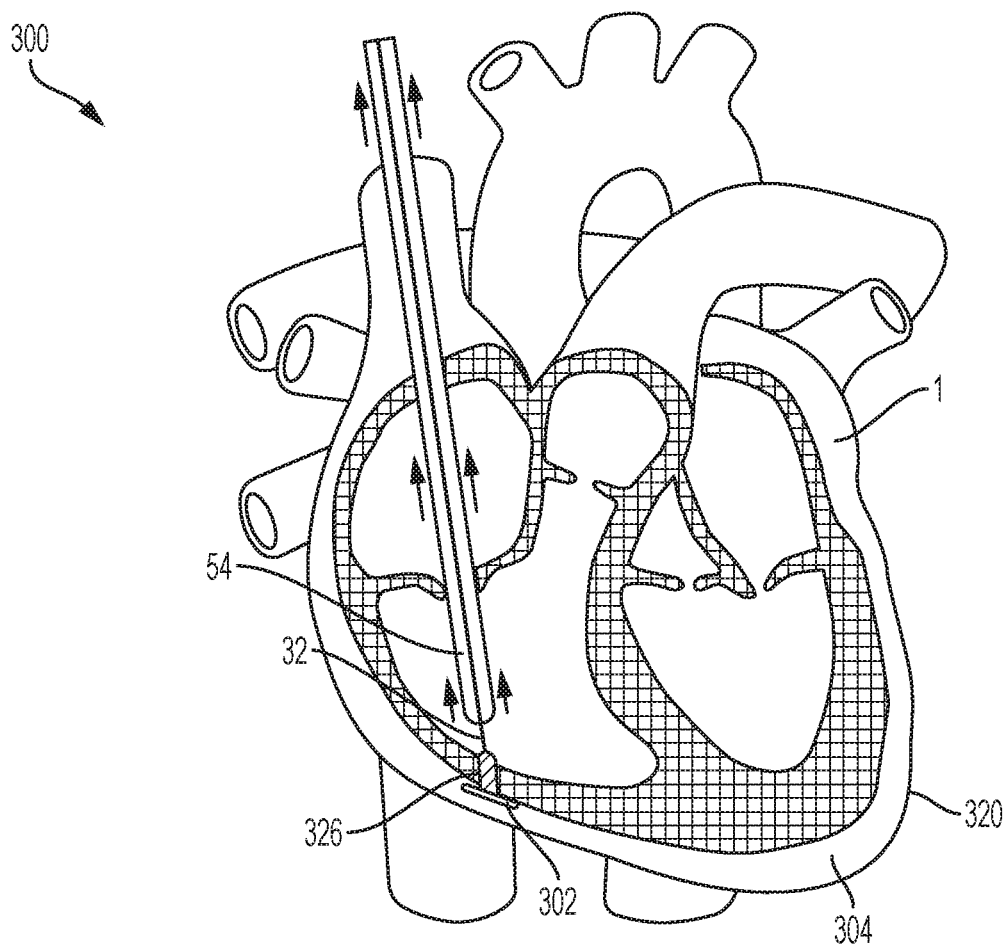
FIG. 14 is a perspective view of the epicardial tether system of FIG. 8, in which an anchor of the system has been deployed in the insufflated pericardial space.

The anchor 302 of the epicardial tether system 300 is coupled to the distal end 64 of the anchor delivery rod 54. In one aspect, the anchor is a self-expanding anchor (that is, the anchor is compressible so that it fits through the inner guide lumen of the anchor delivery guide 52). As illustrated in FIGS. 13 and 14, when the anchor 302 positioned on the distal end of the anchor delivery rod reaches the pericardial space 304, the anchor expands to its full size, thereby locking the anchor 302 in place. A left ventricle portion 326 of the anchor extends through the endocardium and into the left ventricle.

Figure 15:
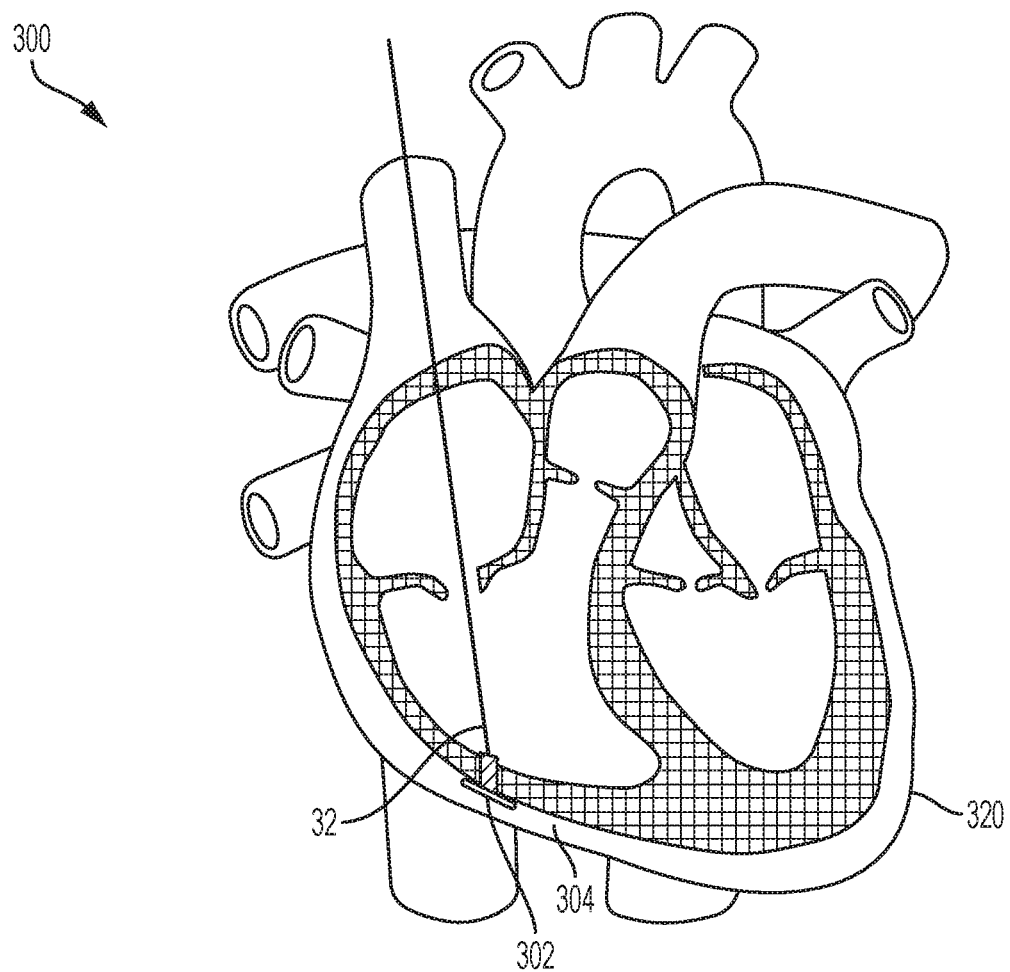
FIG. 15 is a perspective view of the epicardial tether system of FIG. 8, in which an anchor of the system has been deployed in the insufflated pericardial space and delivery devices of the system have been retracted.

In one aspect, the at least one cord 32 is coupled to the anchor 302 prior to deployment in the pericardial space 304. For example, the cord is coupled to the anchor such that the cord is positioned in the inner rod lumen of the anchor delivery rod 54. Thus, when the anchor delivery rod is removed from the heart, as illustrated in FIG. 15, the cord extends from the anchor 302 in the pericardial space through the tricuspid annulus and superior (or inferior) vena cava to outside of the heart. In this aspect, at least the valve 100 and suture 34 are coupled to the cord 32. It is within the scope of the present invention, however, for the anchor to be untethered or uncoupled from the valve upon insertion. As is appreciated, the carbon dioxide in the pericardial space 304 is resorbed and the pericardium returns to its normal position.

The Interventricular Tether System (FIGS. 16-24)

Figure 16:
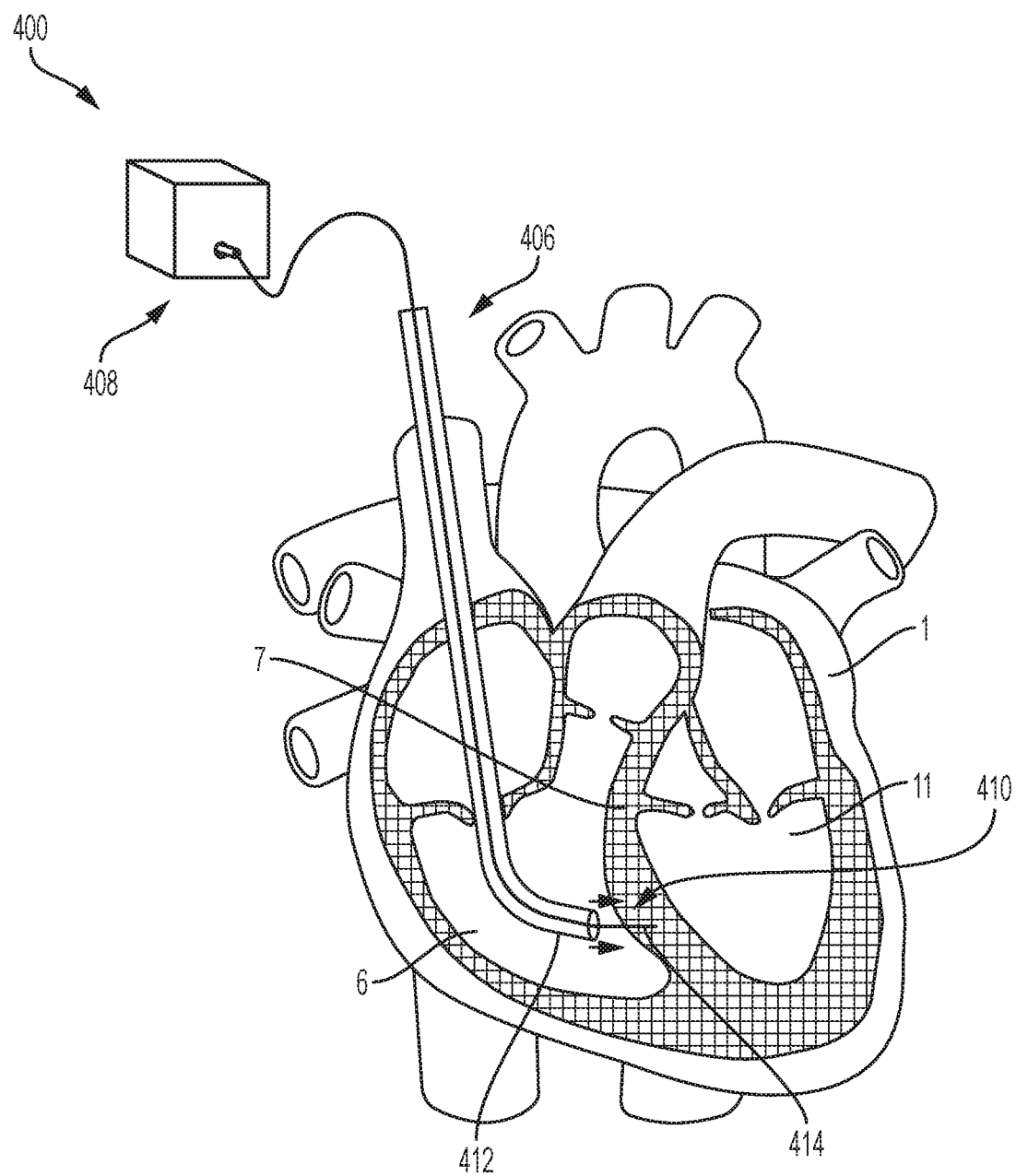
FIG. 16 is a perspective view of an interventricular tether system for positioning an anchor in the left ventricle, according to one aspect.
Figure 17:
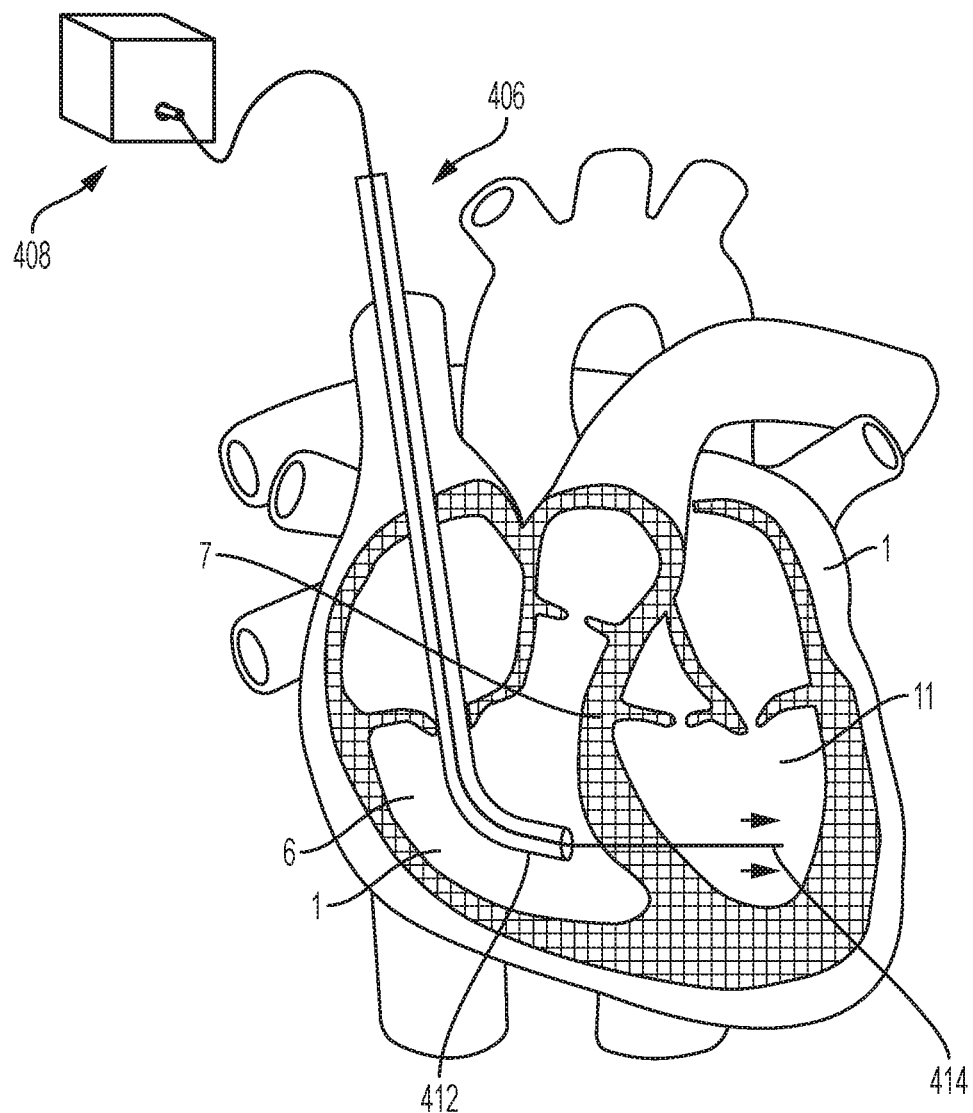
FIG. 17 is a perspective view of the interventricular tether system of FIG. 16, in which an RF wire of the system has crossed the septum and entered the left ventricle.

In another embodiment, illustrated in FIGS. 16-24, the assembly comprises an interventricular tether system 400 for positioning an anchor 402 in the left ventricle 11. In one aspect, the interventricular tether system tether comprises a catheter 406, a radiofrequency ("RF") generator 408 and a RF wire 410 electrically coupled to the RF generator. In another aspect, the catheter is a wire delivery catheter having a distal end 412 configured to be positioned adjacent to or near the septum 7 of the heart 1. In use, RF generated by the RF generator 408 urges a distal end 414 of the RF wire to penetrate the septum, moving from the right ventricle 6 into the left ventricle 11 as shown in FIGS. 16 and 17.

Figure 18:
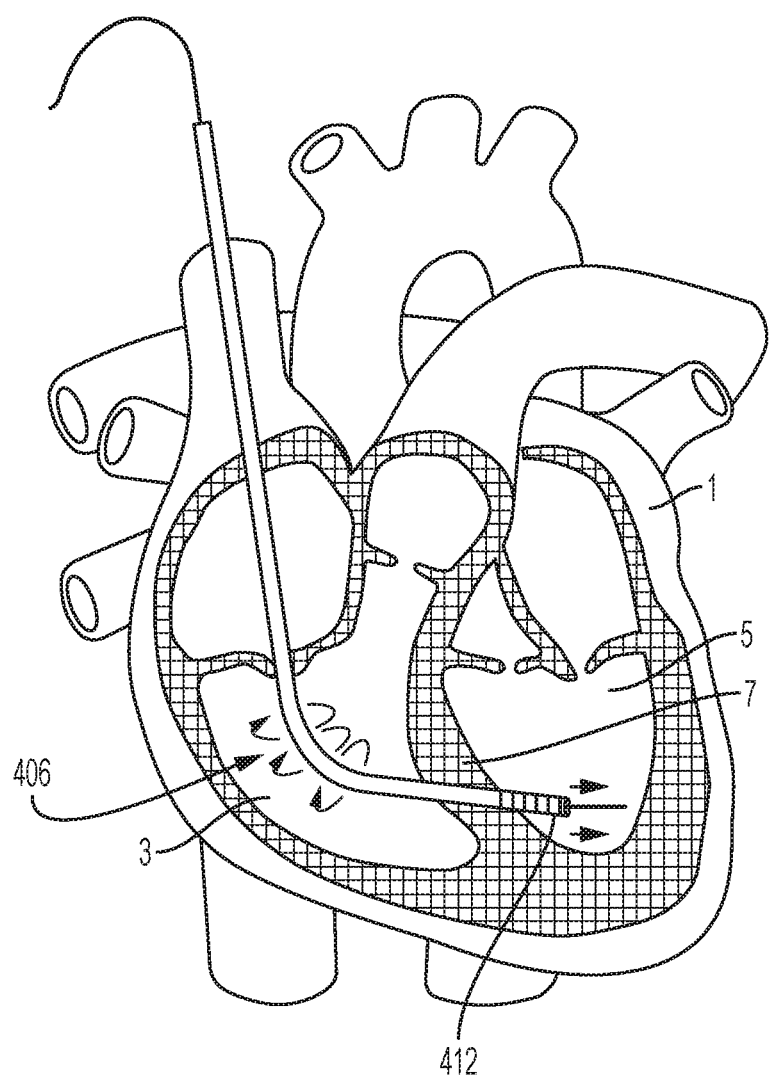
FIG. 18 is a perspective view of the interventricular tether system of FIG. 16, in which a catheter of the system has crossed the septum and entered the left ventricle.
Figure 19:
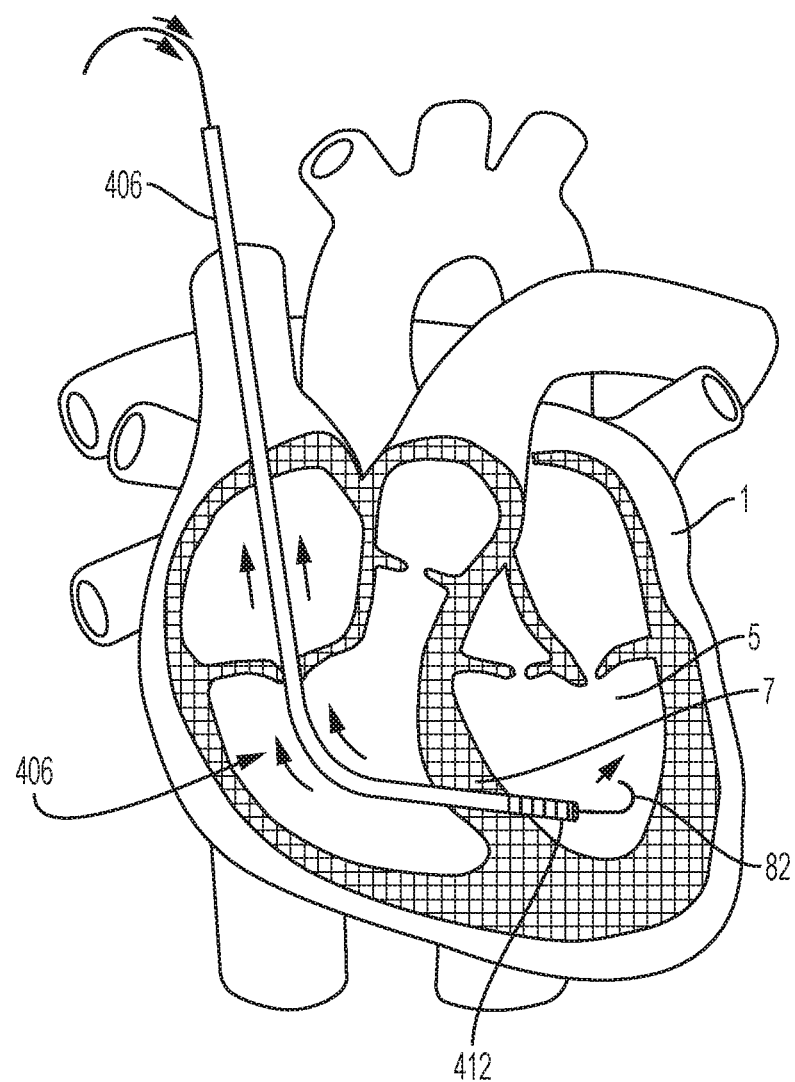
FIG. 19 is a perspective view of the interventricular tether system of FIG. 16, in which a J-wire of the system has been advanced through the catheter and into the left ventricle.

Referring now to FIG. 18, the catheter 406 is then urged into the left ventricle 11. For example, if a portion of the distal end 412 of the catheter is threaded, rotation of the catheter 406 urges the distal end across the septum 7 and into the left ventricle. With a portion of the catheter in the left ventricle, the RF wire is retracted, and the J-wire 82 is inserted through the catheter 406 until a portion of the J-wire is in the left ventricle 11, illustrated in FIG. 19.

Figure 20:
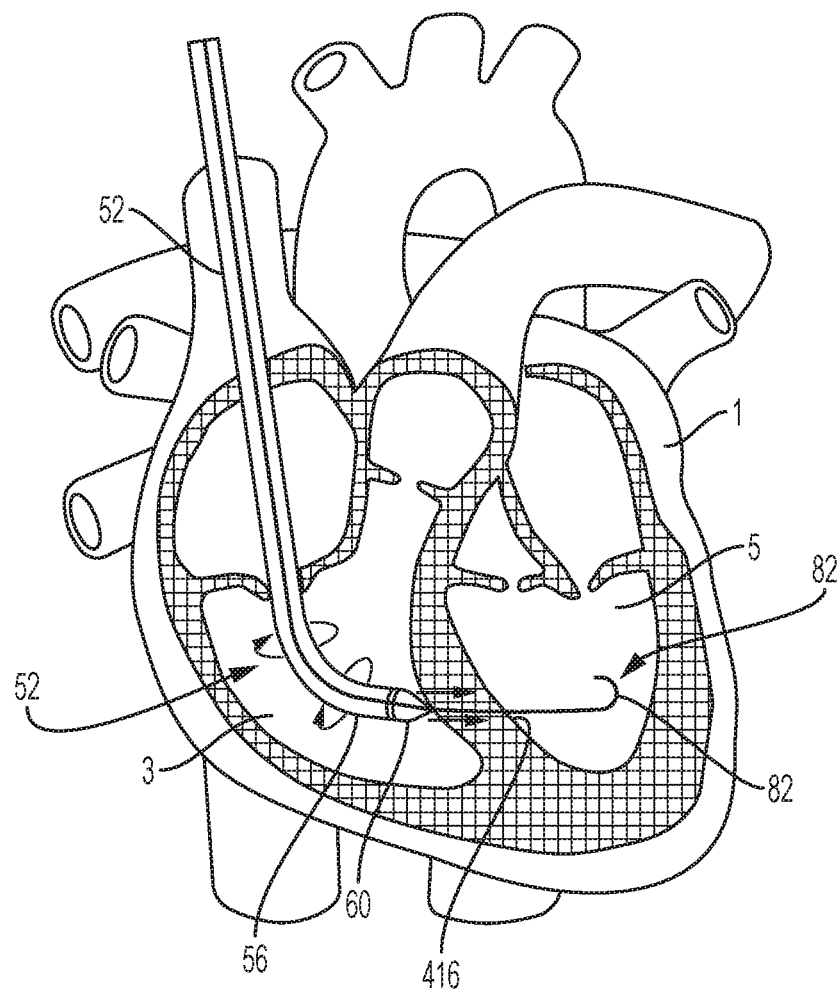
FIG. 20 is a perspective view of the interventricular tether system of FIG. 16, in which a delivery guide of the system approaches the left ventricle.
Figure 21:
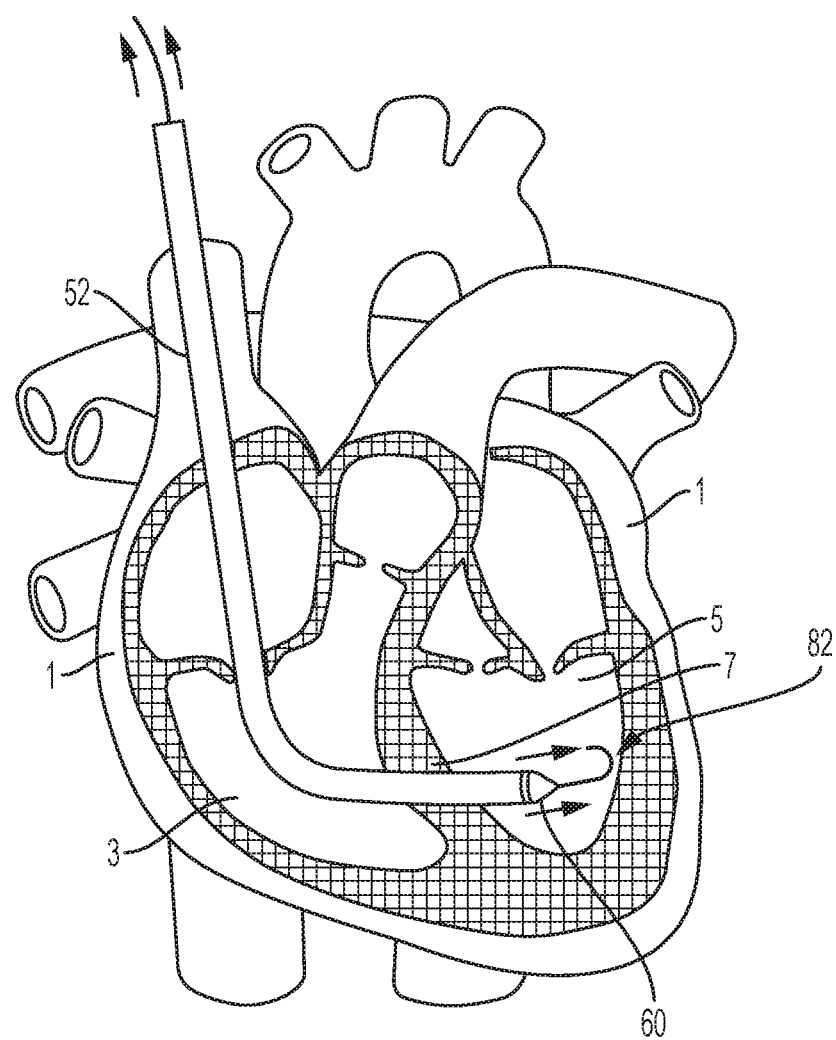
FIG. 21 is a perspective view of the interventricular tether system of FIG. 16, in which the delivery guide of the system has crossed the septum and entered the left ventricle.
Figure 22:
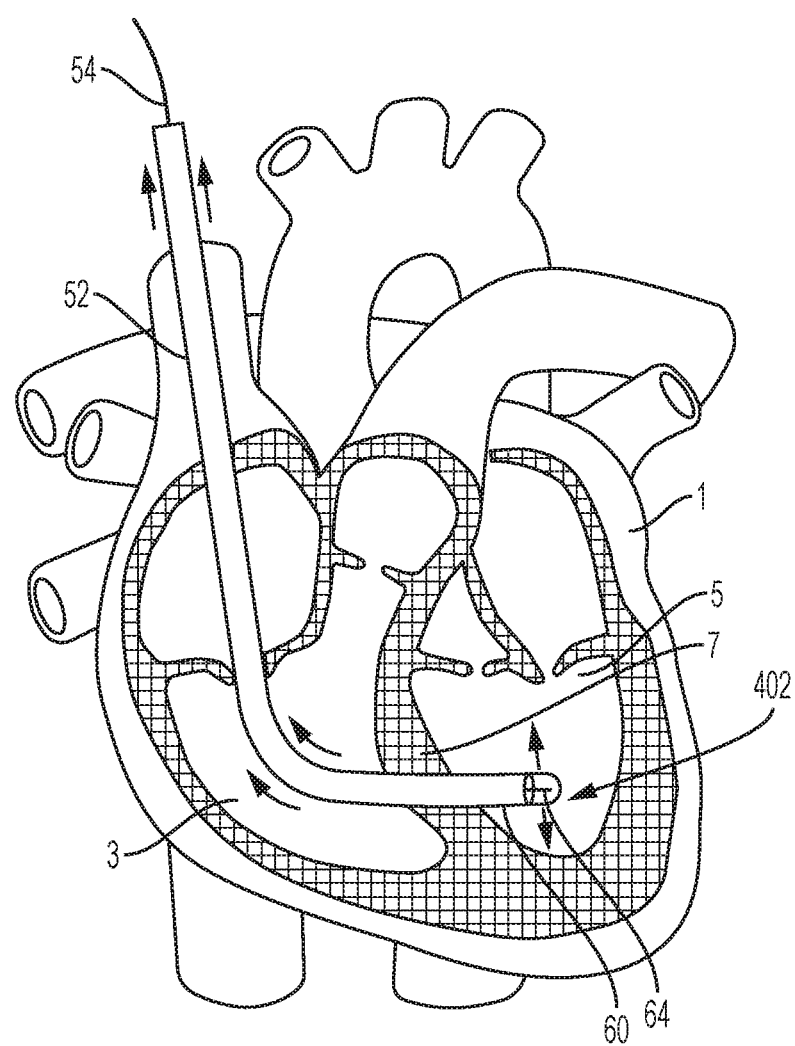
FIG. 22 is a perspective view of the interventricular tether system of FIG. 16, in which an anchor of the system is being positioned in the left ventricle.

In another aspect, illustrated in FIGS. 20 and 21, the anchor delivery guide 52 is inserted over the J-wire 82 until the tip 60 at the distal end 56 of the anchor delivery guide is positioned at or adjacent an anchoring site 416 in the left ventricle 5. The anchor delivery rod 54 is inserted through the inner guide lumen of the anchor delivery guide 52 until the distal end 64 of the anchor delivery rod is positioned in the left ventricle, illustrated in FIG. 22.

Figure 23:
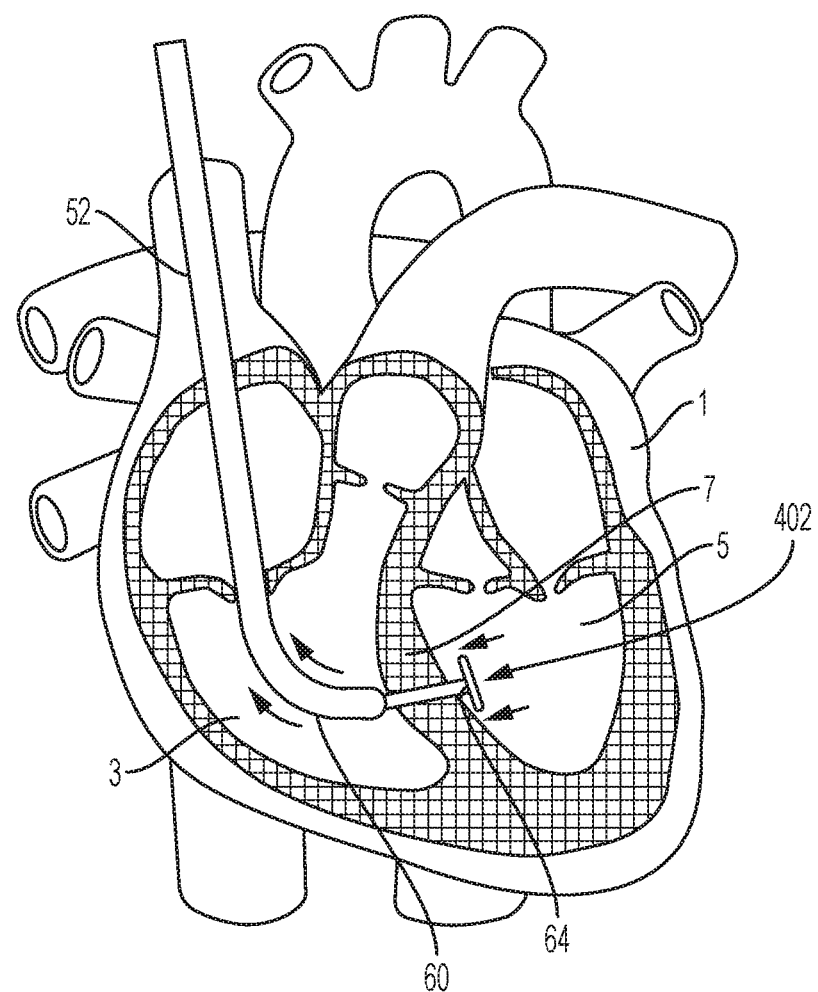
FIG. 23 is a perspective view of the interventricular tether system of FIG. 16, in which an anchor of the system has been deployed in the left ventricle.
Figure 24:
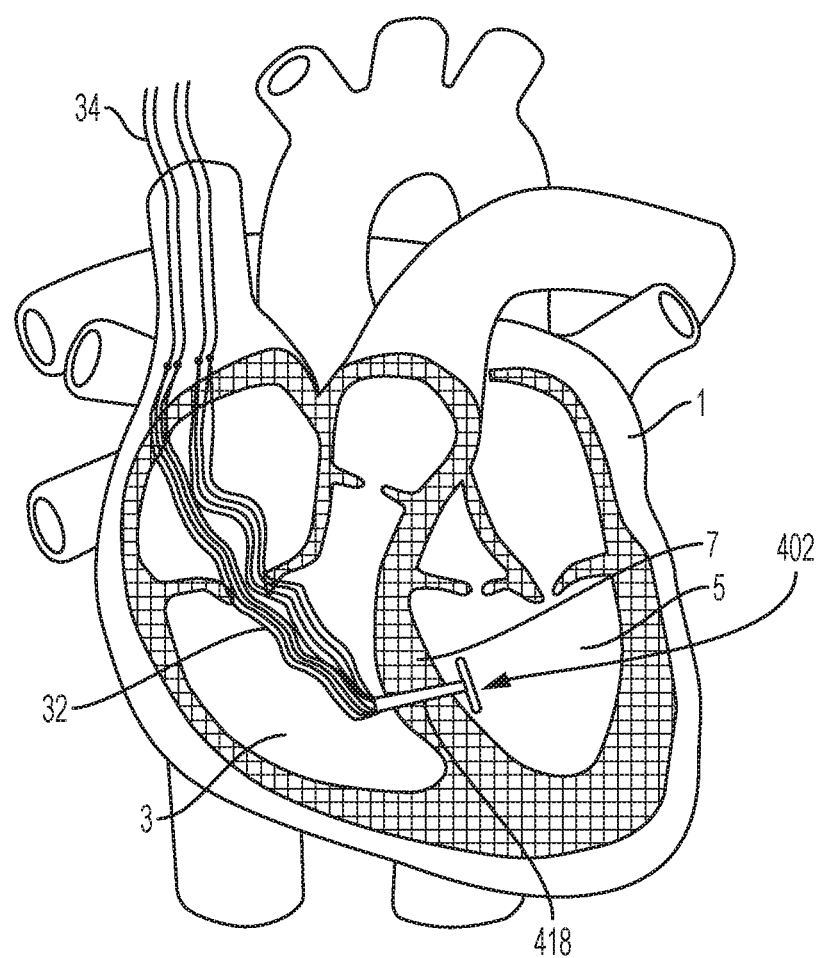
FIG. 24 is a perspective view of the interventricular tether system of FIG. 16, in which an anchor of the system has been deployed in the left ventricle and delivery devices of the system have been retracted.

The anchor 402 of the interventricular tether system 400 is coupled to the distal end 64 of the anchor delivery rod 54. In one aspect, the anchor is a self-expanding anchor (that is, the anchor is compressible so that it fits through the inner guide lumen of the anchor delivery guide 52). As illustrated in FIGS. 23 and 24, when the anchor 402 positioned on the distal end of the anchor delivery rod reaches the left ventricle 11, the anchor exits the inner guide lumen of the anchor delivery guide and expand to its full size, thereby locking the anchor 402 in place. As illustrated in FIG. 24, a right ventricle portion 418 of the anchor extends through the septum 7 and into the right ventricle 6.

In one aspect, the at least one cord 32 is coupled to the right ventricle portion 418 of the anchor 402 prior to deployment in the left ventricle 11. For example, the cord is coupled to the anchor such that the cord is positioned in the inner lumen of the anchor delivery rod 54. Thus, when the anchor delivery rod is removed from the heart 1, as illustrated in FIG. 24, the cord extends from the right ventricle portion of the anchor 402 through the tricuspid annulus. In this aspect then, the valve 12, detachable locks 126, 226 and the like is coupled to the cord 32 as previously described. It is within the scope of the present invention, however, for the anchor to be untethered or uncoupled from the valve upon insertion.

In another aspect, the interventricular anchor 402 is a screw, similar to anchor screw 28, or a fixation mechanism composed of, but not limited to, nitinol, stainless steel, cobalt-chromium, or titanium alloys, in the shape of barbs, hooks, prongs. This type of interventricular anchor could be delivered by the anchor delivery rod 54 via an anchor delivery guide 52.

Figure 26:
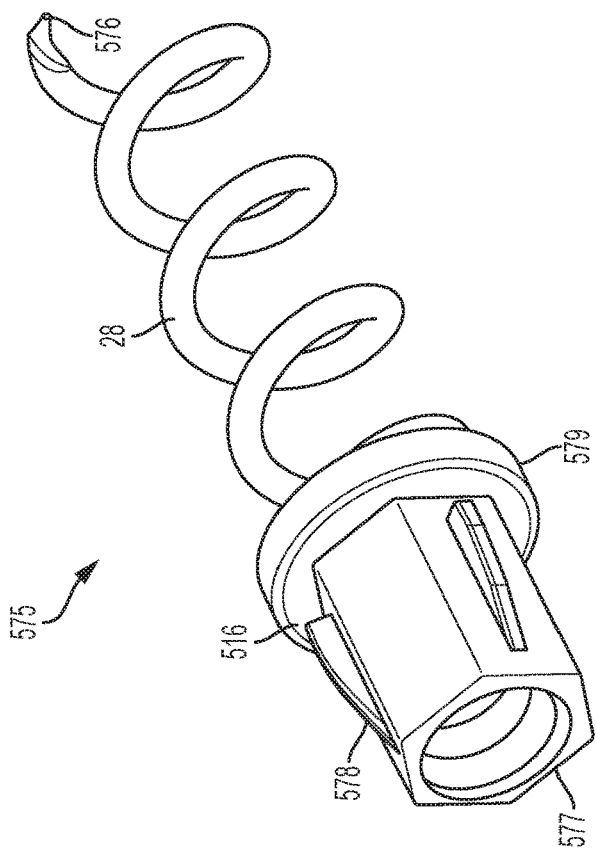
FIG. 26 is a perspective view of an anchor according to another aspect for anchoring a tether to a cardiac wall.
Figure 28:
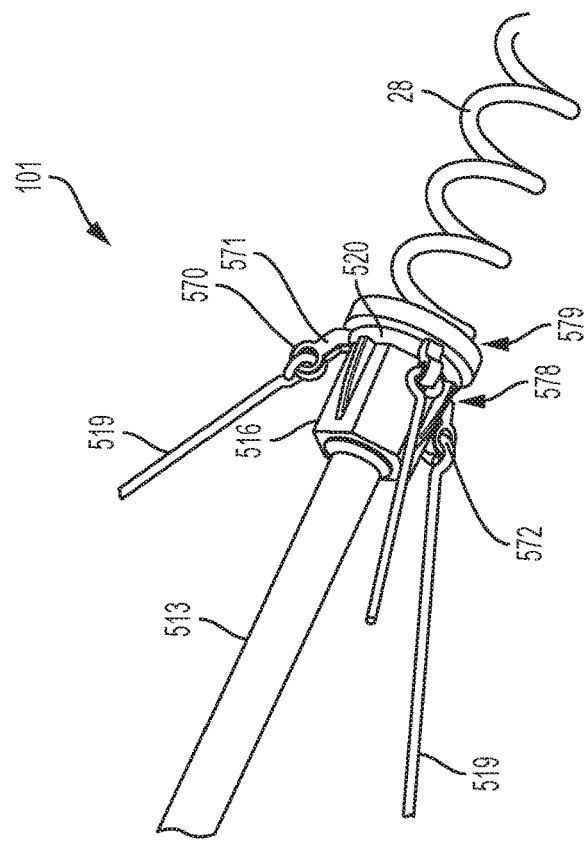
FIG. 28 is a perspective view of the anchor assembly, comprised of the tether, coupled to the anchor, for anchoring the tether to a cardiac wall.
Figure 27:
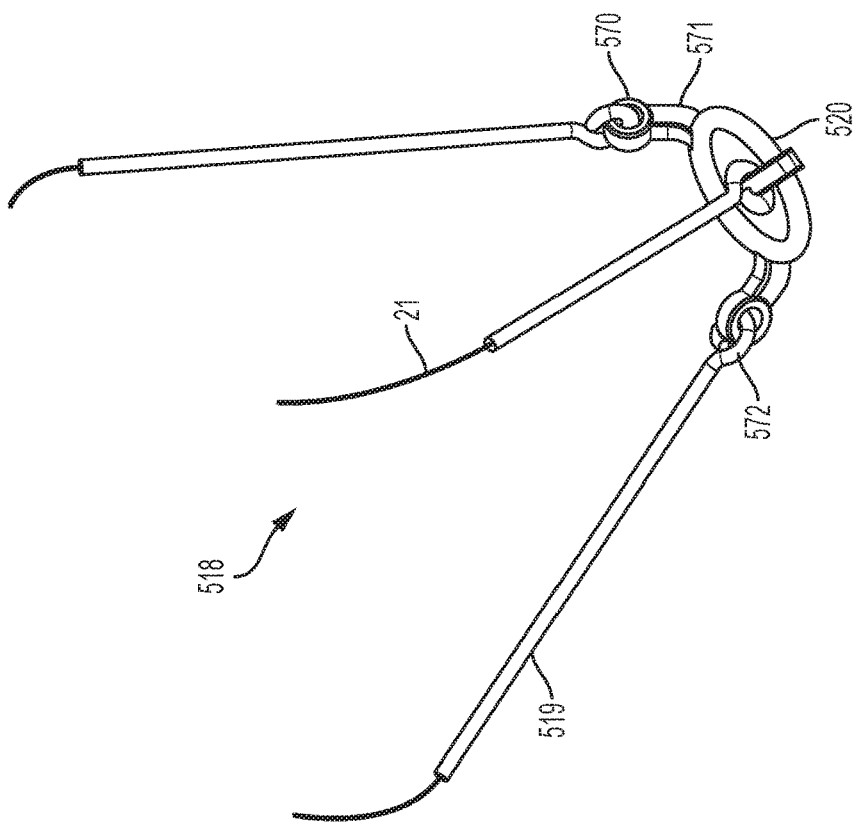
FIG. 27 is a perspective view of a tether assembly for anchoring a valve to the anchor.

The Anchor Assembly (FIGS. 26-28)

According to another aspect of the present invention, the anchor 575 is implanted untethered, that is, it is implanted and then a tether assembly 518 is connected to the anchor 575 and the valve 100. According to this aspect, components of an anchor assembly shown in FIGS. 25-28 include an anchor 575 having an, an anchor cap 30 and a delivery cable 512 allowing delivery of a tether 518. The anchor cap 30 is coupled to the anchor screw 28. The delivery cable 512 is removably connected to the anchor cap 30. The anchor screw 28, as shown, is sized and configured as a helical screw to affix to an intracardiac wall. Optionally, however, the anchor screw 28 may be differentially sized (longer or shorter depending on the cardiac wall to which it attaches) and configured as an inclined plane, nail-like head, or as any other type of screw that would be known to those skilled in the art. In one aspect, the screw is composed of any known metal alloy, including, but not limited to, nitinol, titanium, or cobalt-chromium. In another aspect, the metal alloy of the screw 28 may be coated with biological tissue, such as bovine, ovine, porcine, or equine pericardium, or with any combination of anti-inflammatory drugs that might promote healing and limit inflammation. A tip 576 of the anchor screw 28 optionally is constructed of and/or coated with the same or different materials as the anchor screw 28 and may be fashioned as a blunt or sharp tip.

In use, the anchor 575 is secured to the cardiac wall by rotating the anchor screw 28 until the tip 576 is at a desired depth in the cardiac wall. The depth to which anchor screw 28 is screwed in is adjustable according to the location within the heart. For example, the anchor screw 28 may be implanted more deeply into the interventricular septum, for greater fixation, as opposed to the ventricular free wall, i.e. epicardial wall, where a shallower implantation is safer. By reversing the rotation of the anchor screw 28, the anchor 575 is removed safely from the cardiac wall, either to be repositioned, or to be removed entirely.

The anchor cap 30 comprises at least one locking arm 578 extending radially outwardly from the anchor cap 30. The locking arm 578 is sized and configured for releasably securing a portion of the tether 21 (described below) to the anchor cap 30. The at least one locking arm 578 moves between a first locked position, in which the locking member 578 extends a first distance away from the body of the anchor cap 30, and a second unlocked position in which the locking member 578 extends a second distance away from the anchor cap 30 that is less than the first distance. The anchor cap 30 comprises at least one biasing member (not shown), such as a spring, configured to urge each locking arm 578 to the first locked position. As shown, a plurality of locking arms 578 are provided and are spaced equally around the circumference of the anchor cap 30, though it is contemplated that the locking arms 578 need not be spaced equally.

Figure 25:
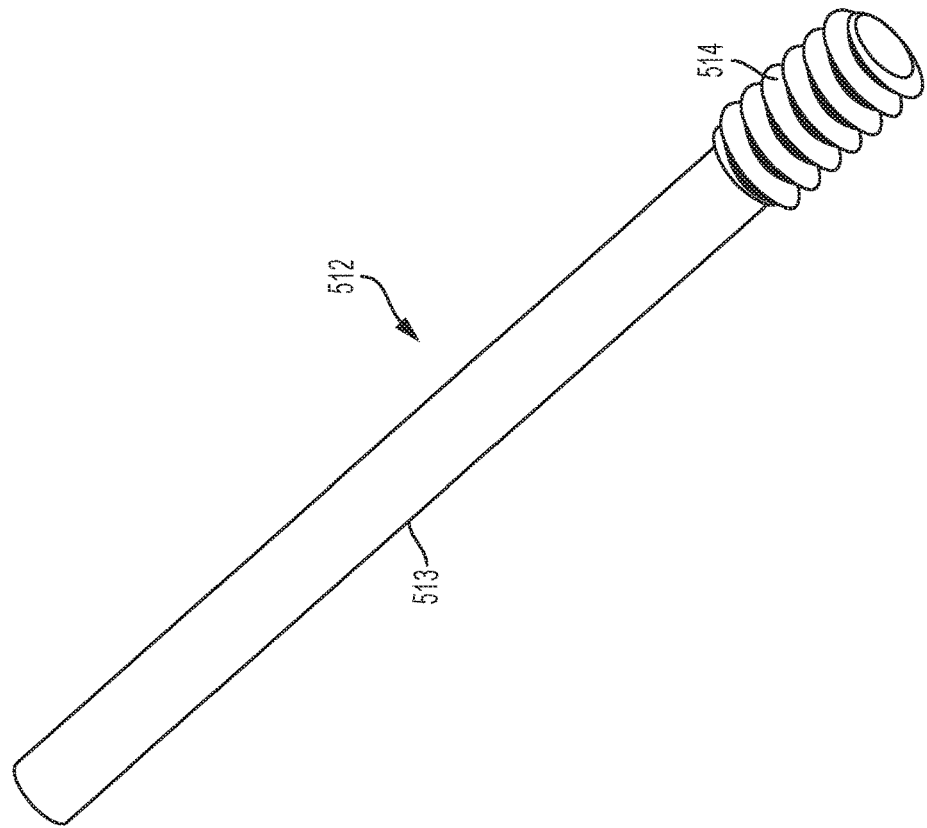
FIG. 25 is a perspective view of the delivery cable of an anchor delivery device for anchoring a tether to a cardiac wall according to another aspect.

Now referring to FIG. 25, the delivery cable 512 includes a flexible delivery wire 513 having a distal threaded end portion 514 positioned on or formed in the distal end of the delivery wire 513. The delivery wire 513 is constructed of, but not limited to, stainless steel, nitinol or other metal alloys, with or without hydrophilic coatings, or with or without a polymer coating such as polytetrafluoroethylene (PTFE). The distal threaded end portion 514 is sized and configured to selectively engage complementary threads formed in a cavity defined in a proximal end 577 of the anchor cap 30. In use, the distal threaded end portion 514 advances, e.g., screws, into via the proximal end 577 of the anchor cap 30 to couple the anchor cap 30 to the distal end of the flexible wire 513. As described more fully below, the distal threaded end portion 514 is unscrewed from the proximal end of the anchor 575, detaching the flexible wire 513 from the anchor 575.

Expanding Anchor Assembly (FIGS. 29A-C)

According to another aspect of the present invention, an expanding anchor assembly 102 is shown in FIGS. 29A-29C. As shown, the anchor assembly 102 is an interventricular anchor such as across the interventricular septum. The anchor assembly 102 includes an anchor cap 516 and locking arm 578 as described above for cooperating with the tether 518. The anchor assembly 102 also includes an anchor shaft 105 having a distal tip 107 configured for penetrating an intracardiac wall. The anchor shaft 105 and anchor screw are comprised of at least two, and as shown three, shaft and anchor sectors 108. The sectors 108 are secured during implantation and intracardiac wall penetration by an internal tensioning means such as tensioning line 109 which splits into at least two or, as shown, three lines 109 terminating at the distal tip 107 of each section 108. Once the distal tip 107 of the anchor shaft 105 enters an intracardiac wall, such as the interventricular septum, the internal tensioning line 109 is released and relaxed, allowing the shaft sectors 108 to separate by the action of internal biasing members (not shown), such as, but not limited to, one or more springs located along one or more inner walls of the shaft sectors 108.

Anchor with Tether Ring (FIGS. 32A-F)

According to another aspect of the disclosure, as shown in FIGS. 32A-F, an anchor assembly 103 is illustrated. The anchor 103 includes an anchor shaft 112 and an anchor screw 114. As shown, the anchor screw 114 has a helical configuration and extends distally from an anchor screw base 115. The anchor screw base 115 defines at least one, or a plurality as shown, of anchor flanges 116 and recessed areas 117 therebetween. The anchor shaft 112 includes at least one or, as shown, a plurality of locking members 118 shown in FIG. 25 B. Locking members 118 are biased, such as by a spring (not shown), radially outwardly from the anchor shaft 112. A delivery cable in the form of an anchor connector 120 and connector rod 121 cooperate with the anchor shaft 112 to rotate the anchor screw 114. The anchor connector 120 defines at least one or, as shown, a plurality of apertures 122 configured for receipt of the anchor flanges 116. Accordingly, the anchor connector 120 and connector rod 121 are matingly connected to the anchor shaft 112, thereby urging the locking members 118 inward. The cooperating of the apertures 122 and the flanges 116 integrate the anchor connector 120 and the anchor screw base 115. Rotation of the connector rod 121 thereby rotates the anchor screw 114 for interventricular or epicardial implantation into an intracardial wall.

Figure 32A:
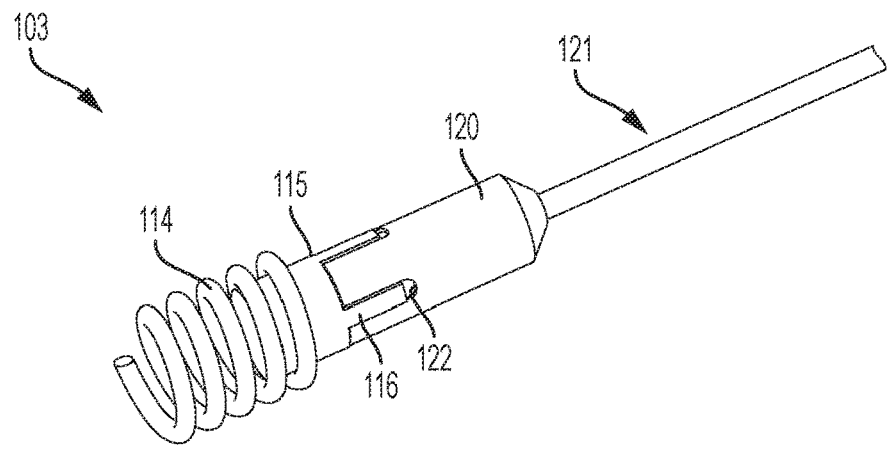
FIGS. 32A-32F are perspective views of an anchor according to another aspect having an anchor screw and anchor cap configured for receipt of connecting ring and a tethering system illustrated in sequential steps.
Figure 32B:
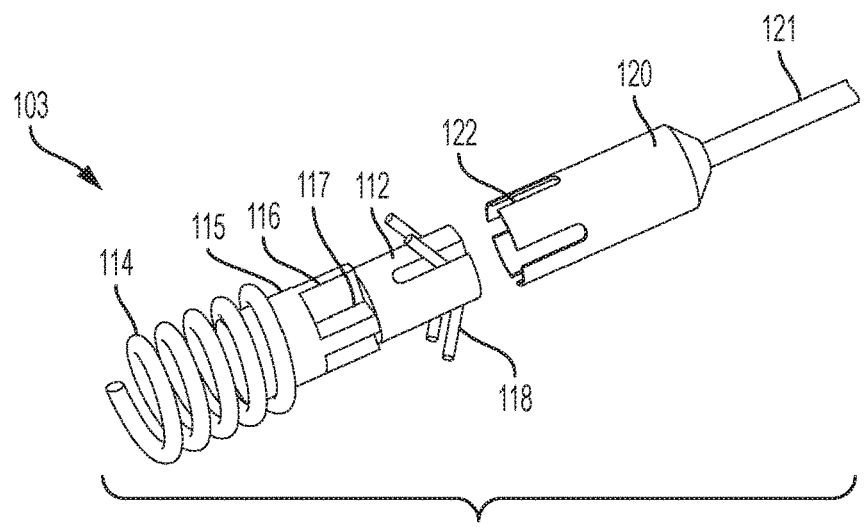
Figure 32C:
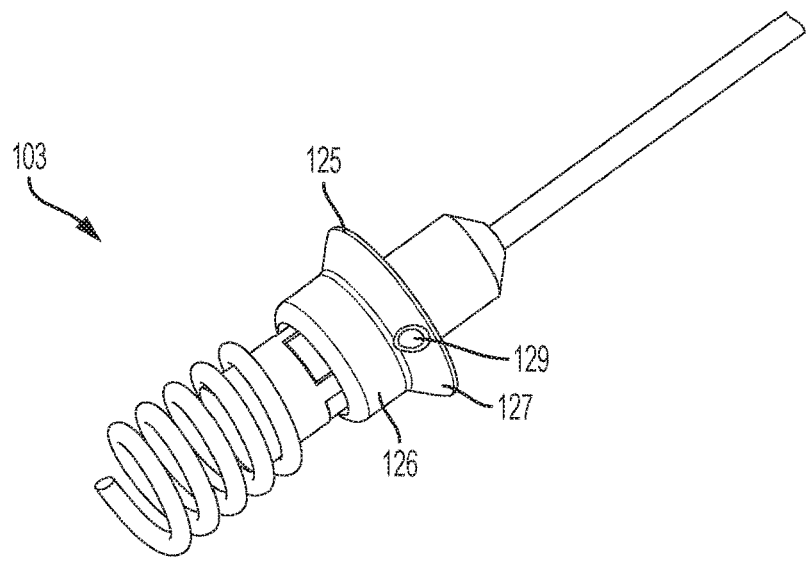
Figure 32D:
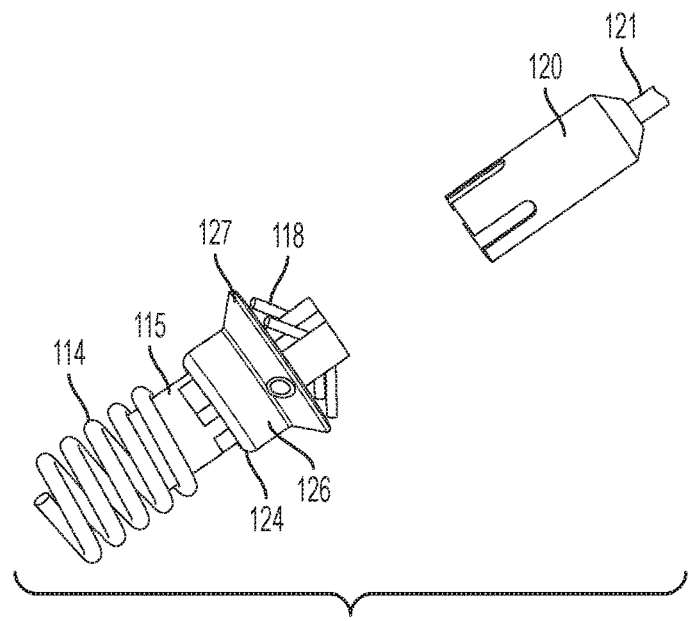
Figure 32E:
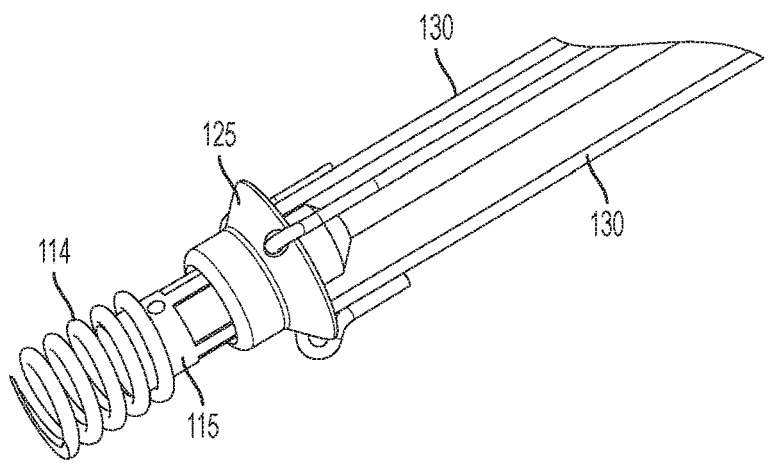
Figure 32F:
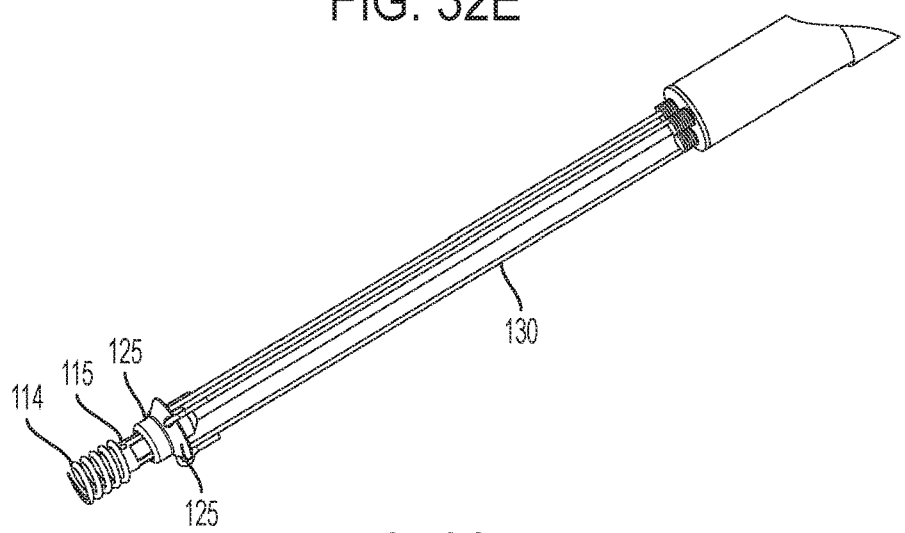

After the anchor screw 114 has been implanted, a tether ring 125 is applied over the connector rod 121 and anchor connecter 120 and abuts the proximal end of the anchor screw 114. The docking or tether ring 125 includes a generally cylindrical first distal portion 126 and a second proximal portion 127 having a diameter greater than the first portion 126. The second portion 127 defines at least one or, as shown, a plurality of apertures 129 configured for receipt of tether rods 130 as shown in FIGS. 32E and 32F. As shown in FIG. 32D, the anchor connector 120 and connector rod 121 are removed. The locking members 118 are urged radially outward so as to engage the second portion 127 of the tether ring 125 to lock the tether ring 125 on the anchor screw base 115. Tether rods 130 are operative as described above for cooperating with an atrial sealing skirt 46.

The Tether Assembly for an Anchor Implanted Untethered

With any of the aforementioned anchors which are implanted without a tether (that is, not pre-connected), a tether assembly is provided to enable the anchor 75/575 to tether to the valve 100. For example, as shown in FIGS. 27 and 28, when the flexible wire 513 is coupled to the anchor 75/575, the flexible wire serves as a guide rail for the advancement of the tether assembly 518 to the anchor 75/575. The tether assembly 518 includes one or more tether rods 519 rotatably connected to a docking ring 520. The tether rods 519 are connected to an eyelet 570 defined by docking ring arms 571 as shown in FIG. 27. The tether assembly 518 is advanced over the flexible wire 513 of the delivery cable 512, and the docking ring 520 of the tether assembly depresses the at least one locking arm 578 of the anchor cap 30/516 to the second unlocked position. With the locking arm 578 in the second position, the docking ring 520 advances over the locking arm 578 on the anchor cap 30 or 516 until the docking ring 520 abuts and/or is adjacent to a distal end 579 of the anchor cap 30 or 516. At this point, the biasing member of the anchor cap 30/516 urges the at least one locking arm 578 to the first locked position, thereby releasably coupling the docking ring 520, and thus the rest of the tether assembly 518, to the anchor 75/575.

In one aspect, when coupled to the anchor 75 or 575, the tether assembly 518 rotates about a longitudinal axis of the anchor a full 360 degrees. Optionally, in another aspect, the tether assembly 518 may be constrained to lesser degrees of rotation by interaction of a portion of the tether assembly 518 with the at least one locking arm 578.

As shown in FIG. 28, in one aspect, the tether assembly 518 comprises at least one docking ring arm 571 coupled to the docking ring 520, and at least one tether rod 519 coupled a docking ring arm 571. As shown, a distal end of the docking ring arm 571 is securely coupled to or formed monolithically with the docking ring 520. As shown, the at least one docking ring arm comprises a plurality of docking ring arms 571. As shown, the plurality of docking ring arms 578 are spaced equally around the circumference of the docking ring, though it is contemplated that the docking ring arms 571 need not need spaced equally. An eyelet 570 is defined by the docking ring arm 571. The tether rod 519 includes a tether rod hook 572 configured for cooperating with the eyelet 570.

A proximal end of each docking ring arm 571 is rotatably coupled to a distal end of a respective tether rod 519. A tether rod hook 572 is defined by the tether rod 519 as shown and is either coupled to or formed monolithically with the distal end of each tether rod 519. In another aspect, the eyelet 570 and the tether rod hook 572 are sized and configured so that the tether rod hook 572 is inserted into the eyelet 570 to securely, rotatably couple the tether rod 519 to the docking ring 520. In use, each tether rod hook 572 rotates about the circumference of the eyelet 570. As shown in FIG. 27, the proximal end of each tether rod is coupled to a cord 21. The tether rod 519 and the tether rod hook 572 may be composed of any metal alloy.

The tether assembly 518 is configured to cooperate with any intracardiac anchor including, but not limited to, the interventricular and epicardial anchors disclosed herein and the interventricular and epicardial anchors of Applicants' prior disclosure incorporated herein by reference.

The Anchor Delivery Device for an Untethered Anchor

Figure 30A:
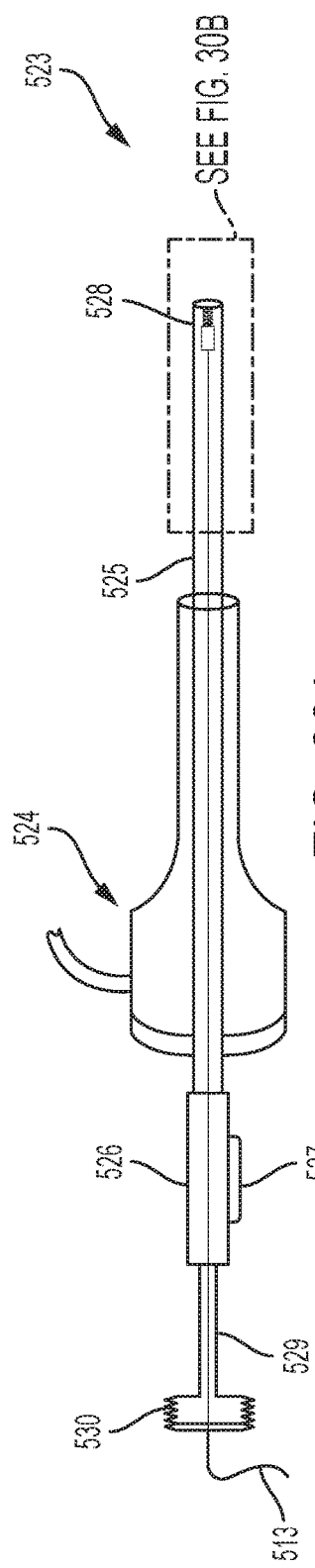
FIG. 30A is a side elevational view of the anchor delivery device.
Figure 30B:
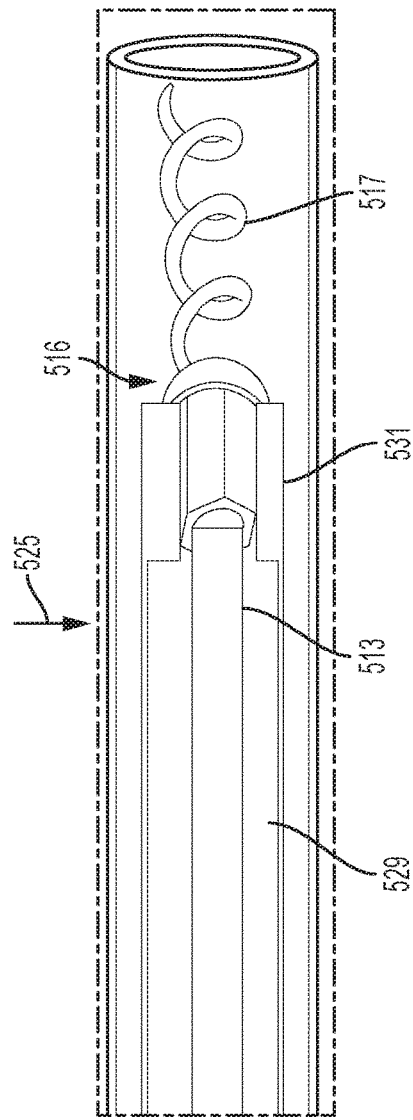
FIG. 30B is a side view of the anchor delivery device shown within the delivery sheath.
Figure 30C:
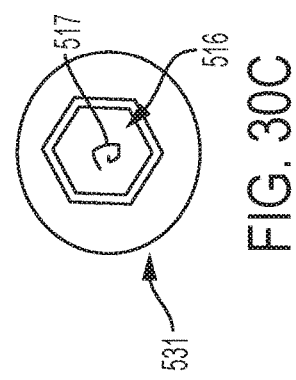
FIG. 30C is an end view of the anchor delivery device.

Referring now to FIGS. 30A-30 C and 31A-31B, the anchor delivery device 523 for positioning and deploying the anchor cap 516 (or 30) at the desired position is illustrated and pertains to the components of anchor assembly utilizing the tether assembly with an anchor 75 implanted without a tether. The delivery device 523 comprises an anchor delivery guide 525 and an anchor delivery rod 529. The anchor delivery guide has a distal end 528 and an inner guide lumen sized and configured so that at least one portion of the anchor delivery rod 529 extends there through. At least a portion of anchor delivery guide 525 is flexible so that the distal end 528 of the anchor delivery guide 525 is positioned at or adjacent to an intracardiac wall.

The anchor delivery rod 529 is configured to securely attach the anchor screw 517 to the intracardiac wall 7. The anchor delivery rod 529 has a distal end 531, an opposed proximal rotating handle 530, and an inner rod lumen extending there between. The inner rod lumen is sized and configured so that at least a portion of the delivery cable 512 extends there through. At least a portion of the anchor delivery rod 529 is flexible so that a rod tip 531 at the distal end of the anchor delivery rod 529 may be positioned at or adjacent the intracardiac wall 7.

A portion of the anchor cap 516/30 (as shown, the portion proximal to the anchor cap distal end 579) is received by and extends within the anchor rod tip 531. The outer configuration of the anchor cap 516 proximal portion includes a firsts surface configuration and the inner wall configuration of said anchor rod 529 distal portion has a second configuration wherein the first and second configuration mate. Thus, when the anchor cap 516/30 is positioned in and engaged with the anchor rod tip 531, rotation of the anchor delivery rod 529 rotates the anchor cap 516/30. In this position, the anchor screw 28 extends distally from the anchor delivery rod 529 as illustrated in FIG. 30B and the delivery cable 512 extends through the inner rod lumen of the anchor delivery rod 529.

The anchor delivery device 523 also includes a guide handle 526 having a deflection knob 527 coupled to the anchor delivery guide 525. The guide handle 526 and the deflection knob 527 are configured and used to help guide the distal end 528 of the anchor delivery guide 525 to the intracardiac wall 7. A rod handle 530 is coupled to the anchor delivery rod 529 wherein rotation of the rod handle rotates the rod tip 531 and the anchor cap 516 when the anchor cap is positioned in the anchor rod tip 531.

As shown, in FIG. 30A a sheath 524 is configured to receive the anchor delivery guide 525. The sheath 524 is in fluid communication with the anchor delivery guide so that fluids, such as heparinized saline and the like surrounds the anchor delivery guide through the sheath 524. A central sheath channel 533 (FIG. 31B) is defined in the sheath 524 to provide communication with the inner guide lumen of the anchor delivery guide 525 for the anchor delivery rod 529 and other system components to extend through the central sheath channel 533.

The Method of Implanting the Untethered Anchor

Figure 31B:
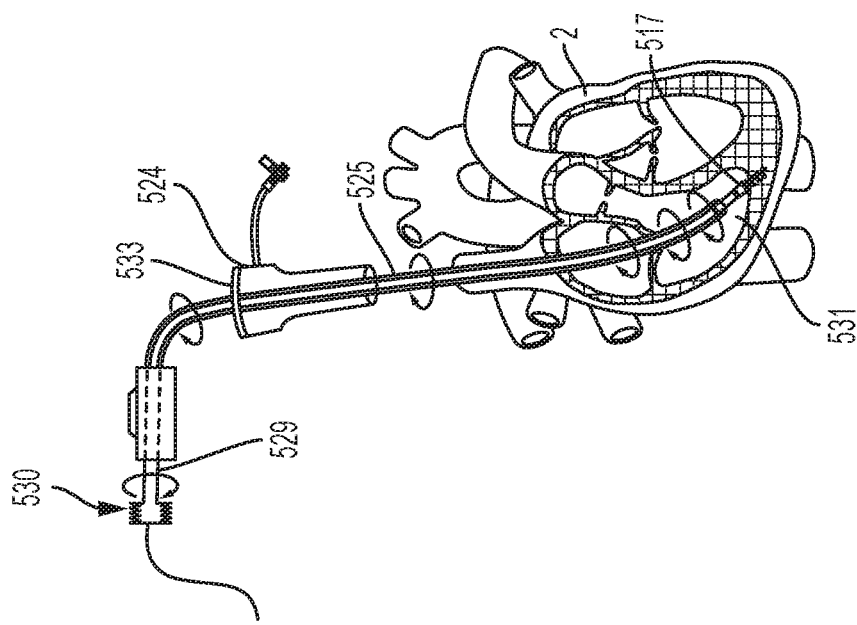
FIG. 31B is a perspective view of the anchor being implanted into the intracardiac wall.
Figure 31A:
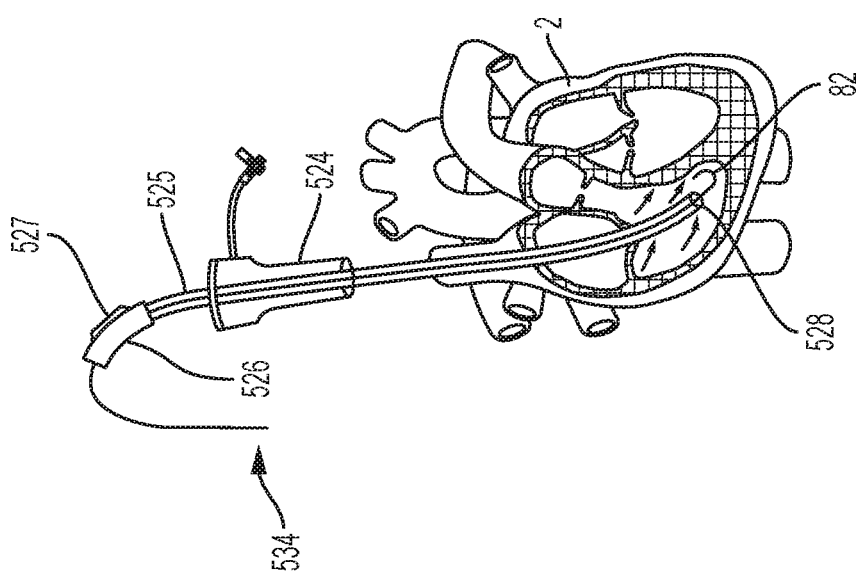
FIG. 31A is a perspective view of the anchor delivery device being positioned in the right ventricle.

As shown in FIG. 31A, in the tricuspid annulus, for example, a J-wire 82 is endovascularly guided by the user to the intracardiac wall 7. The anchor delivery device or system 523 is then guided over the J-wire until the distal end 528 of the anchor delivery guide 525 is positioned at or adjacent the intracardiac wall 7. FIGS. 31A-B illustrate the anchor assembly implanted into an intracardiac wall that is an endocardial wall. Anchor assembly 101 may also be implanted into an interventricular wall. The J-wire is, for example and without limitation, a 0.025" or 0.035" J-wire. Of course, J-wires having other diameters are contemplated. The anchor cap 516/30 is coupled to the distal end 531 of the anchor delivery rod 529. The anchor delivery rod 529 is then be inserted through the inner guide lumen of the anchor delivery guide 525 until the anchor cap 516/30 and the distally extending anchor screw 28 (or sectors 108) are positioned at or adjacent the intracardiac wall 7.

The anchor assembly 102 of FIGS. 29A-29C may also be implanted and guided by the J-wire 82 such as into the interventricular wall as the intracardiac wall 7 shown. The anchor assembly 103 of FIGS. 32A-F may also be implanted and guided by the J-wire 82 into an intracardiac wall 7, such as an interventricular wall or an epicardial wall.

With the anchor screw 28 (or sectors 108) of anchors systems 101, 102 or 103 positioned adjacent to the intracardiac wall 7, the rotating handle 530 of the anchor delivery rod 529 or 121 is rotated to cause corresponding rotation of the anchor cap 516/30 as illustrated in FIG. 31B. For example, the rotating handle 530 is rotated in a first direction to cause corresponding rotation of the anchor cap 516. The anchor screw 28 (or 108) coupled to the anchor cap 516/30 also rotates and screws into a portion of the intracardiac wall until the anchor cap 516/30 is adjacent to the apex wall. Note that in this position, the anchor screw 28 (or 108) may or may not extend completely through any intracardiac wall, but trans-apical access is not necessary. Upon placement of the anchor cap 516 in the desired position, the anchor delivery rod 529 and the anchor delivery guide 525 are retracted from the heart 2. After placement of the anchor cap 516/30, the flexible wire 513 of the delivery cable 512 extends from the anchor cap 516, through the tricuspid annulus, and through the right atrium 3.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An intracardiac anchor assembly for minimally invasively anchoring a cardiac device to a cardiac wall at an anchor implantation site by endovascular insertion and implantation and for tethering the cardiac device to an anchor, said anchor assembly comprising:

an anchor cap configured and sized for endovascular introduction for implanting the anchor to an intracardiac wall at the implantation site having a proximal and distal end;

an anchor screw extending from said anchor cap distal end and configured for penetration a predetermined distance into the intracardiac wall at the implantation site;

at least one mating member on said anchor cap, said at least one mating member being selectively moved from a first position to a second position;

a removable anchor delivery cable sized and configured for endovascular introduction and having a distal end configured to mate with said anchor cap proximal end to removably couple the removable anchor delivery cable to the anchor cap; and a tether assembly comprising a docking ring configured to be inserted over said anchor cap wherein said docking ring mates with said at least one mating member of said anchor cap to secure said docking ring to said anchor cap wherein, when said removeable anchor delivery cable is removed from said anchor cap, said docking ring comprises at least one tether for tethering the cardiac device to said docking ring.

2. The intracardiac anchor assembly according to claim 1 wherein said at least one mating member is a locking arm biased so as to extend radially outwardly from said anchor cap.

3. The intracardiac anchor assembly according to claim 2 wherein said anchor comprises at least two of said locking arms.

4. The intracardiac anchor assembly according to claim 1 wherein said anchor screw is a helical screw.

5. The intracardiac anchor assembly according to claim 1 wherein said predetermined distance is a distance sufficient to penetrate and exit an intracardiac wall at said implantation site.

6. The intracardiac anchor assembly according to claim 5 further comprising:
   an anchor shaft having a distal end for penetrating the intracardiac wall and a distal portion and extending from the anchor cap distal end and said anchor screw extends circumferentially around said anchor shaft wherein said distal portion of said anchor shaft defines at least two anchor sectors including a respective portion of said anchor screw; and
   tensioning means operatively connected to said anchor sectors wherein said tensioning means is released and said anchor sectors are configured to expand when exiting an opposing side of the intracardiac wall so as to anchor said anchor assembly.

7. The intracardiac anchor assembly according to claim 6 wherein said tensioning means is a tensioning line extending through said anchor shaft and said line includes at least two distal lines for connecting to a respective one of said at least two anchor sectors.

8. The intracardiac anchor assembly according to claim 6 wherein said anchor cap has a first outer surface configuration on at least its proximal end and said anchor assembly comprises an anchor delivery rod having a distal end defining a distal cavity having a second interior configuration which is configured to mate with and engage said anchor cap first surface configuration for implanting said anchor cap at said implantation site.

9. The intracardiac anchor assembly according to claim 1 wherein said tether assembly further comprises at least one docking ring arm extending from said docking ring.

10. The intracardiac anchor assembly according to claim 9 wherein said at least one docking ring arm is operatively connected to a cord which extends from a proximal end of said at least one docking ring arm.

11. The intracardiac anchor assembly according to claim 9 wherein said at least one docking ring arm comprises at least two docking ring arms.

12. The intracardiac anchor assembly according to claim 9 wherein said at least one docking ring arm is rotatably coupled to said docking ring.

13. The intracardiac anchor assembly according to claim 1 wherein said anchor cap has a first outer surface configuration on at least its proximal end and said anchor assembly comprises an anchor delivery rod having a distal end defining a distal cavity having a second interior configuration which is configured to mate with and engage said anchor cap first surface configuration for implanting said anchor cap at said implantation site.

14. The intracardiac anchor assembly according to claim 1 wherein said anchor comprises an anchor shaft defining a first surface configuration and said anchor screw extends distally from said anchor shaft.

15. The intracardiac anchor assembly according to claim 14 wherein said removable anchor delivery cable comprises a removable anchor connector and a connector rod connected to said anchor connector, said anchor connector having a second surface configuration wherein said second surface configuration and said anchor shaft first surface configuration are mating surfaces.

16. The intracardiac anchor assembly according to claim 15 wherein said anchor connector maintains the at least one mating member in said second position when mated with said anchor shaft.

17. The intracardiac anchor assembly according to claim 16 wherein said docking ring is configured for receipt of said anchor connector and connector rod and for cooperating with said at least one anchor cap mating member when said anchor connector is removed so as to be locked in position on said anchor shaft, said docking ring defining coupling means to engage said cap mating member.

18. The intracardiac anchor assembly according to claim 15 wherein said anchor shaft first surface configuration includes at least one flange and recess and said anchor connector second surface configuration includes at least one mating recess and flange for coupling with said anchor shaft.

19. The intracardiac anchor assembly according to claim 14 wherein said tether assembly comprises at least two tether rods and wherein said tether rods are removably connected to said docking ring.

20. The intracardiac anchor assembly according to claim 1 wherein said docking ring of said tether assembly comprises an aperture configured to be implanted over said anchor cap so as to extend circumferentially around said anchor cap.

21. The intracardiac anchor assembly according to claim 20 wherein said tether assembly is rotatably coupled to said anchor cap.

22. The intracardiac anchor assembly according to claim 1 wherein said tether of docking ring comprises at least one tether rod and a cord is operatively connected to and extending from a proximal end of said at least one tether rod.

\* \* \* \* \*